United States Patent
Huang et al.

(10) Patent No.: US 9,519,141 B2
(45) Date of Patent: Dec. 13, 2016

(54) CORRESPONDENCE RELATION SPECIFYING METHOD FOR ADAPTIVE OPTICS SYSTEM, ADAPTIVE OPTICS SYSTEM, AND STORAGE MEDIUM STORING PROGRAM FOR ADAPTIVE OPTICS SYSTEM

(71) Applicant: HAMAMATSU PHOTONICS K.K., Hamamatsu-shi, Shizuoka (JP)

(72) Inventors: Hongxin Huang, Hamamatsu (JP); Takashi Inoue, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 14/895,521

(22) PCT Filed: May 29, 2014

(86) PCT No.: PCT/JP2014/064295
§ 371 (c)(1),
(2) Date: Dec. 3, 2015

(87) PCT Pub. No.: WO2014/196449
PCT Pub. Date: Dec. 11, 2014

(65) Prior Publication Data
US 2016/0124221 A1    May 5, 2016

(30) Foreign Application Priority Data
Jun. 6, 2013 (JP) .................................. 2013-119858

(51) Int. Cl.
*A61B 3/02* (2006.01)
*A61B 3/00* (2006.01)
(Continued)

(52) U.S. Cl.
CPC ......... *G02B 27/0068* (2013.01); *A61B 3/1015* (2013.01); *A61B 3/13* (2013.01);
(Continued)

(58) Field of Classification Search
USPC .................................................. 351/200–246
See application file for complete search history.

(56) References Cited

U.S. PATENT DOCUMENTS

| 4,305,666 A | 12/1981 | Becherer et al. | |
| 2014/0146286 A1* | 5/2014 | Suzuki | A61B 3/117 351/206 |
| 2015/0085255 A1* | 3/2015 | Thaung | A61B 3/1015 351/214 |

FOREIGN PATENT DOCUMENTS

| CN | 102944932 | 2/2013 |
| JP | H09-15057 A | 1/1997 |

(Continued)

OTHER PUBLICATIONS

International Preliminary Report on Patentability dated Dec. 17, 2015 for PCT/JP2014/064295.

*Primary Examiner* — Mohammed Hasan
(74) *Attorney, Agent, or Firm* — Drinker Biddle & Reath LLP

(57) ABSTRACT

An adaptive optics system includes a spatial light modulator configured to spatially modulate a phase of an optical image incident on a modulation surface including N two-dimensionally arranged regions and a wavefront sensor including a lens array having N two-dimensionally arranged lenses corresponding to the N regions and an optical detection element for detecting a light intensity distribution including M converging spots formed by the lens array and configured to receive the optical image after the modulation from the spatial light modulator, and compensates for the wavefront distortion by controlling a phase pattern displayed in the (Continued)

spatial light modulator based on a wavefront shape of the optical image obtained from the light intensity distribution, wherein a correspondence relation between the region of the spatial light modulator and the converging spot formed in the wavefront sensor is specified while the compensation for the wavefront distortion is executed.

9 Claims, 22 Drawing Sheets

(51) Int. Cl.

| | |
|---|---|
| *A61B 3/14* | (2006.01) |
| *G02B 27/00* | (2006.01) |
| *G01M 11/02* | (2006.01) |
| *G02F 1/1335* | (2006.01) |
| *G02F 1/1362* | (2006.01) |
| *G01J 9/00* | (2006.01) |
| *G02F 1/01* | (2006.01) |
| *A61B 3/10* | (2006.01) |
| *A61B 3/13* | (2006.01) |
| *G01J 1/42* | (2006.01) |
| *G02B 27/09* | (2006.01) |

(52) U.S. Cl.
CPC ...... *A61B 3/14* (2013.01); *G01J 1/42* (2013.01); *G01J 9/00* (2013.01); *G01M 11/02* (2013.01); *G01M 11/0264* (2013.01); *G02B 27/0927* (2013.01); *G02F 1/01* (2013.01); *G02F 1/0121* (2013.01); *G02F 1/133553* (2013.01); *G02F 1/136277* (2013.01); *G02F 2201/346* (2013.01); *G02F 2203/12* (2013.01); *G02F 2203/18* (2013.01)

(56) References Cited

FOREIGN PATENT DOCUMENTS

| | | |
|---|---|---|
| JP | 2009-162614 A | 7/2009 |
| JP | 2009-192832 | 8/2009 |
| JP | 2009-244030 | 10/2009 |
| JP | 2010-201810 | 9/2010 |
| JP | 2010-530615 A | 9/2010 |
| JP | 2010-261810 A | 11/2010 |

* cited by examiner

Fig.9
(a)
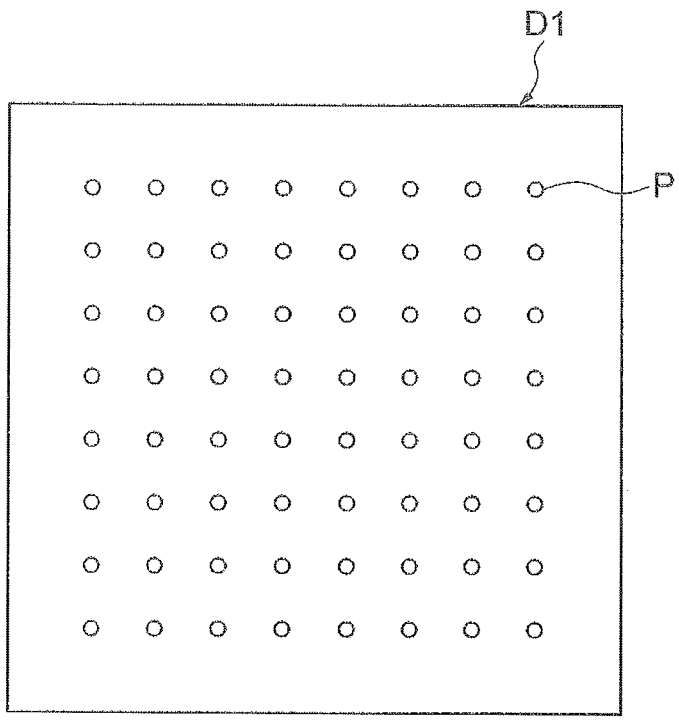
(b)
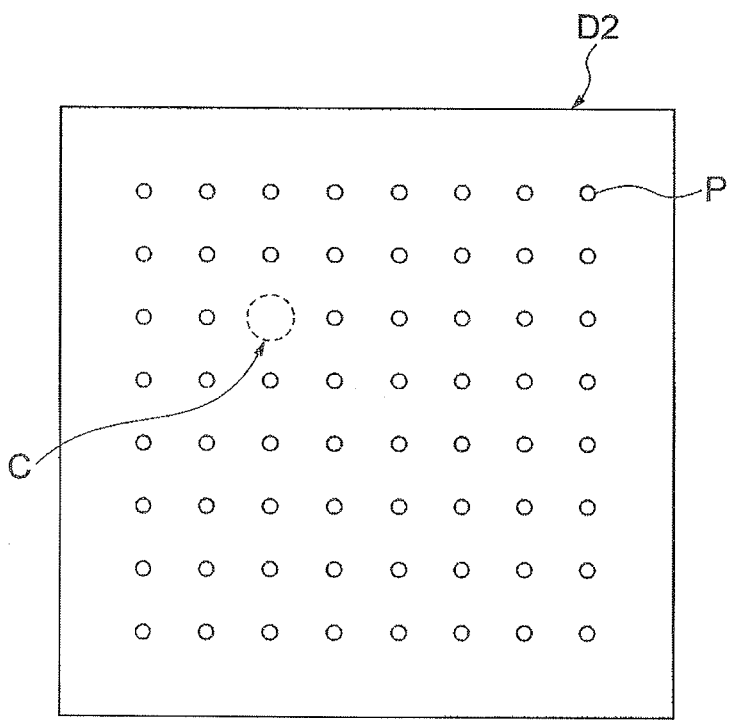

CORRESPONDENCE RELATION SPECIFYING METHOD FOR ADAPTIVE OPTICS SYSTEM, ADAPTIVE OPTICS SYSTEM, AND STORAGE MEDIUM STORING PROGRAM FOR ADAPTIVE OPTICS SYSTEM

TECHNICAL FIELD

An aspect of the present invention relates to a correspondence relation specifying method for an adaptive optics system, an adaptive optics system, and a storage medium storing a program for an adaptive optics system.

BACKGROUND ART

In Patent Literature 1, technology related to a wavefront sensor for measuring a wavefront of light waves is disclosed. In the wavefront sensor, a characteristic (for example, light intensity) is applied to light passing through each of a plurality of lenses and image data is obtained from a light receiving element such as a CCD receiving the light. A measurement spot position is calculated from this image data, a characteristic of a converging spot is detected, a reference spot position corresponding to the converging spot having the characteristic and the measurement spot position are associated, and a wavefront is calculated from the associated reference spot position and measurement spot position.

CITATION LIST

Patent Literature

[Patent Literature 1] Japanese Unexamined Patent Publication No. H9-15057

SUMMARY OF INVENTION

Technical Problem

Adaptive optics technology is technology for dynamically removing an aberration by measuring an optical aberration (wavefront distortion) using a wavefront sensor and controlling a wavefront modulation element (spatial light modulator) based on a measurement result. It is possible to improve an imaging characteristic, a degree of convergence, an SN ratio of an image, and measurement precision through the above-described adaptive optics technology. Conventionally, the adaptive optics technology was mainly used in astronomical telescopes and large laser apparatuses. In recent years, the adaptive optics technology has been applied to ocular fundus cameras, scanning laser ophthalmoscopes, optical coherence tomography apparatuses, laser microscopes, etc. Imaging using such adaptive optics technology enables observation at high resolution that was previously unavailable. For example, the ocular aberration is removed by applying the adaptive optics technology to an ocular fundus imaging apparatus for observing the back (ocular fundus) of the eye. For example, it is possible to clearly draw a microstructure of the ocular fundus such as a visual cell, a nerve fiber, or a capillary. The adaptive optics technology can be applied to the early diagnosis of diseases concerning the circulatory system as well as ocular diseases.

An adaptive optics system for implementing the above-described adaptive optics technology is mainly constituted of a spatial light modulator, a wavefront sensor, and a control apparatus for controlling the spatial light modulator and the wavefront sensor. For example, it is possible to use a wavefront sensor (so-called Shack-Hartmann wavefront sensor) that includes a plurality of two-dimensionally arranged lenses and adopts a scheme of measuring the wavefront based on positional displacement from the reference position of the converging spot formed by each lens as the wavefront sensor.

In this adaptive optics system, it is important to accurately know a correspondence relation between a plurality of lenses of the wavefront sensor and a plurality of detected converging spots. FIG. 22 is a diagram illustrating a correspondence relation between a plurality of lenses 101 and a plurality of converging spots P when an optical image having a certain wavefront W is incident on the wavefront sensor. As shown in FIG. 22(a), the converging spot P formed by the corresponding lens 101 is located inside a plurality of regions 104 on a detection surface 103 opposite to the plurality of lenses 101 because an amount of positional displacement of each converging spot P is small when an aberration of the wavefront W is small. In this case, the aberration in the region is calculated based on a distance (an amount of positional displacement) between the position of the converging spot to be formed when the aberration of the wavefront W is zero, that is, a reference position, and a position of the converging spot P formed within the same region 104 as the reference position.

However, when the aberration of the wavefront W is large as illustrated in FIG. 22(b), the following problems occur. That is, because an amount of positional displacement of the converging spot P becomes large in such a case, the converging spot P may be located outside the region 104 opposite to the lens 101 which forms the converging spot P. Therefore, a situation in which there is no converging spot P in a certain region 104 and there are a plurality of converging spots P in another region 104 may occur. In addition, when the wavefront W is largely inclined as illustrated in FIG. 22(c), the converging spot P formed by each lens 101 may be located within a region 104 adjacent to a region 104 opposite to each lens 101.

Because a correspondence relation between the converging spot P and the lens 101 is unclear in the situation illustrated in FIG. 22(b) or 22(c), it is difficult to specify a region on the modulation surface of the spatial light modulator to be controlled based on the position of the converging spot P. Therefore, the precision of wavefront distortion compensation is degraded or a magnitude of wavefront distortion capable of being compensated for is limited. For example, when an adaptive optics system is applied to an ocular fundus imaging apparatus, an ocular aberration may significantly differ according to each measurement target person and the aberration may increase according to an ocular position or a position of an optical system for correcting near- or far-sightedness. In these cases, the above-described problems appear.

Also, in the scheme disclosed in Patent Literature 1, there are the following problems. In Patent Literature 1, a scheme of arranging an optical plate having a thickness differing according to each region corresponding to one lens before the lens, a scheme of arranging an optical plate having transmittance differing according to each region corresponding to one lens before the lens, and a scheme of arranging a liquid crystal shutter before the lens are shown as schemes of applying the characteristic to light passing through each of the plurality of lenses of the wavefront sensor. However, in these schemes, the optical plate or the like is newly arranged on an optical path of light to be measured and the number of components increases. Because loss occurs in light to be measured when the light passes through the optical plate or the like, the precision of wavefront detection may be degraded. Also, even when a mechanism capable of inserting and removing the optical plate or the like is provided according to necessity, it is difficult to adjust a relative position with the lens and a size of an apparatus increases.

An aspect of the present invention has been made in view of such problems and an objective of the invention is to provide a correspondence relation specifying method for an adaptive optics system, an adaptive optics system, and a storage medium storing a program for an adaptive optics system that can precisely compensate for larger wavefront distortion by accurately specifying a correspondence relation between a converging spot of a wavefront sensor and a region on a modulation surface of a spatial light modulator to be controlled based on a position of the converging spot in a simple configuration while an increase of loss of light to be measured is controlled.

Solution to Problem

According to an aspect of the present invention for solving the above-described problems, there is provided a correspondence relation specifying method for an adaptive optics system, which includes a spatial light modulator configured to spatially modulate a phase of an optical image incident on a modulation surface including N (N is a natural number) two-dimensionally arranged regions and a wavefront sensor including a lens array having N two-dimensionally arranged lenses corresponding to the N regions and an optical detection element for detecting a light intensity distribution including M (M is a natural number and M≤N) converging spots formed by the lens array and configured to receive the optical image after the modulation from the spatial light modulator and measure a wavefront shape of the optical image based on the light intensity distribution and which compensates for wavefront distortion by controlling a phase pattern displayed in the spatial light modulator based on the wavefront shape of the optical image obtained from the light intensity distribution, wherein a correspondence relation between the region of the spatial light modulator and the converging spot formed in the wavefront sensor is specified while the compensation for the wavefront distortion is executed, the correspondence relation specifying method including: a first detecting step of detecting the light intensity distribution through the optical detection element in a state in which a phase pattern for compensating for the wavefront distortion is displayed in a specific target region among the N regions of the spatial light modulator, a second detecting step of detecting the light intensity distribution through the optical detection element in a state in which a spatially non-linear phase pattern is displayed in the specific target region before or after the first detecting step; and a first specifying step of specifying a converging spot corresponding to the specific target region among the M converging spots based on a change in the light intensity distribution between the first detecting step and the second detecting step.

In the above-described method, in the adaptive optics system including the spatial light modulator and the wavefront sensor, as the first detecting step, the light intensity distribution is detected in the optical detection element of the wavefront sensor in a state in which the phase pattern for compensating for the wavefront distortion is displayed in the specific target region of the spatial light modulator. In the first detecting step, the converging spot corresponding to the specific target region is formed at any position on the optical detection element. Also, as the second detecting step before or after the first detecting step, the light intensity distribution is detected in the optical detection element of the wavefront sensor in the state in which the spatially non-linear phase pattern is displayed in the specific target region. In this second detection step, light diverges due to a non-linear phase pattern displayed in the specific target region and the converging spot corresponding to the specific target region is not formed or its light intensity is weakened.

Thereafter, there is a clear converging spot corresponding to the specific target region in the light intensity distribution obtained in the first detecting step when the light intensity distributions obtained in the first detecting step and the second detecting step are compared with each other in the first specifying step, but there is no converging spot corresponding to the specific target region in the light intensity distribution obtained in the second detecting step or the clarity of the converging spot is significantly degraded as compared with the first detecting step. Accordingly, it is possible to accurately specify the converging spot corresponding to the specific target region based on the change in the light intensity distribution between the first detecting step and the second detecting step.

As described above, according to the above-described correspondence relation specifying method, it is possible to accurately specify the correspondence relation between the converging spot of the wavefront sensor and the region on the modulation surface of the spatial light modulator to be controlled based on the aberration calculated from the position of the converging spot. Accordingly, it is possible to precisely compensate for larger wavefront distortion. In addition, according to the above-described correspondence relation specifying method, it is possible to prevent the number of components from increasing because it is unnecessary to add a new component such as an optical plate like that in the configuration disclosed in Patent Literature 1, and it is possible to maintain the precision of wavefront detection by suppressing an increase of loss of light to be measured.

The correspondence relation specifying method for the adaptive optics system may further include: a third detecting step of detecting the light intensity distribution through the optical detection element in a state in which the phase pattern for compensating for the wavefront distortion is displayed in the specific target region and the spatially non-linear phase pattern is displayed in a specific target region separate from the specific target region; and a second specifying step of specifying a converging spot corresponding to the separate specific target region based on a change in the light intensity distribution between the second detecting step and the third detecting step. According to this method, it is possible to efficiently specify the correspondence relation between each region and the converging spot while sequentially displaying the spatially non-linear phase pattern in a plurality of regions of the spatial light modulator.

Also, in the correspondence relation specifying method for the adaptive optics system, in the first detecting step, the phase pattern for compensating for the wavefront distortion may be displayed in all of the N regions. Even in this method, it is possible to specify the correspondence relation between the specific target region of the spatial light modulator and the converging spot.

Also, in the correspondence relation specifying method for the adaptive optics system, the wavefront distortion may be compensated for based on the wavefront shape obtained from the light intensity distribution detected in the second detecting step. That is, in this method, the wavefront distortion is compensated for based on the wavefront shape measured in the state in which the spatially non-linear phase pattern is displayed in the specific target region. In this case, the phase pattern for compensating for the wavefront distortion is not displayed in the specific target region. However, it is possible to suppress an influence by the specific target region and sufficiently compensate for the wavefront distortion by limiting the specific target region to a small number of parts among the N regions of the spatial light modulator. In addition, in this case, a phase pattern from which a part corresponding to the specific target region in the measured wavefront shape is excluded may be used when the phase pattern to be displayed in the spatial light modulator is calculated.

Also, in the correspondence relation specifying method for the adaptive optics system, the spatially non-linear phase pattern (that is, a phase pattern having a spatially non-linear phase profile) displayed in the specific target region in the second detecting step may include a random distribution in which a distribution of magnitudes of phases is irregular. Alternatively, in the correspondence relation specifying method for the adaptive optics system, the spatially non-linear phase pattern displayed in the specific target region in the second detecting step may include a defocus distribution which increases a diameter of the converging spot. The phase pattern includes any distribution among these distributions, so that it is possible to implement the spatially non-linear phase pattern.

Also, in the correspondence relation specifying method for the adaptive optics system, a plurality of regions which are not adjacent to each other among the N regions of the spatial light modulator may be set in the specific target region. Thereby, because it is possible to specify a correspondence relation between a plurality of specific target regions of the spatial light modulator and a plurality of converging spots at one time, it is possible to shorten a time required to specify the correspondence relation.

Also, according to an aspect of the present invention, there is provided an adaptive optics system including: a spatial light modulator configured to spatially modulate a phase of an optical image incident on a modulation surface including N (N is a natural number) two-dimensionally arranged regions; a wavefront sensor including a lens array having N two-dimensionally arranged lenses corresponding to the N regions and an optical detection element for detecting a light intensity distribution including M (M is a natural number and M≤N) converging spots formed by the lens array and configured to receive the optical image after the modulation from the spatial light modulator and measure a wavefront shape of the optical image based on the light intensity distribution; and a control unit configured to compensate for the wavefront distortion by controlling a phase pattern displayed in the spatial light modulator based on the wavefront shape of the optical image obtained from the light intensity distribution, wherein the control unit acquires a first light intensity distribution through the light detection element in a state in which a phase pattern for compensating for the wavefront distortion is displayed in a specific target region among the N regions of the spatial light modulator while the compensation for the wavefront distortion is executed, acquires a second light intensity distribution through the optical detection element in a state in which a spatially non-linear phase pattern is displayed in the specific target region, and specifies a converging spot corresponding to the specific target region among the M converging spots based on a change between the first light intensity distribution and the second light intensity distribution.

According to this adaptive optics system, the control unit acquires the light intensity distribution in each of the state in which the phase pattern for compensating for the wavefront distortion is displayed in the specific target region of the spatial light modulator and the state in which the spatially non-linear phase pattern is displayed in the specific target region. Accordingly, as in the above-described correspondence relation specifying method, it is possible to accurately specify the converging spot corresponding to the specific target region based on a change between the light intensity distributions and improve the precision of wavefront distortion compensation. In addition, it is possible to prevent the number of components from increasing because it is unnecessary to add a new component such as an optical plate and maintain the precision of wavefront detection by suppressing an increase of loss of light to be measured.

Also, there is provided a program for an adaptive optics system, which includes a spatial light modulator configured to spatially modulate a phase of an optical image incident on a modulation surface including N (N is a natural number) two-dimensionally arranged regions, a wavefront sensor including a lens array having N two-dimensionally arranged lenses corresponding to the N regions and an optical detection element for detecting a light intensity distribution including M (M is a natural number and M≤N) converging spots formed by the lens array and configured to receive the optical image after the modulation from the spatial light modulator, and a control unit configured to compensate for the wavefront distortion by controlling a phase pattern displayed in the spatial light modulator based on a wavefront shape of the optical image obtained from the light intensity distribution, wherein the program for the adaptive optics system causes the control unit to specify a correspondence relation between the region of the spatial light modulator and the converging spot formed in the wavefront sensor while the compensation for the wavefront distortion is executed, the program for the adaptive optics system causing the control unit to execute: a first detecting step of detecting the light intensity distribution through the optical detection element in a state in which a phase pattern for compensating for the wavefront distortion is displayed in a specific target region among the N regions of the spatial light modulator; a second detecting step of detecting the light intensity distribution through the optical detection element in a state in which a spatially non-linear phase pattern is displayed in the specific target region before or after the first detecting step; and a first specifying step of specifying a converging spot corresponding to the specific target region among the M converging spots based on a change in the light intensity distribution between the first detecting step and the second detecting step.

Also, according to an aspect of the present invention, there is provided a storage medium storing a program for an adaptive optics system, which includes a spatial light modulator configured to spatially modulate a phase of an optical image incident on a modulation surface including N (N is a natural number) two-dimensionally arranged regions, a wavefront sensor including a lens array having N two-dimensionally arranged lenses corresponding to the N regions and an optical detection element for detecting a light intensity distribution including M (M is a natural number and M≤N) converging spots formed by the lens array and configured to receive the optical image after the modulation from the spatial light modulator and measure a wavefront shape of the optical image based on the light intensity distribution, and a control unit configured to compensate for the wavefront distortion by controlling a phase pattern displayed in the spatial light modulator based on the wavefront shape of the optical image obtained from the light intensity distribution, wherein the program for the adaptive optics system causes the control unit to specify a correspondence relation between the region of the spatial light modulator and the converging spot formed in the wavefront sensor while the compensation for the wavefront distortion is executed, the program for the adaptive optics system causing the control unit to execute: a first detecting step of detecting the light intensity distribution through the optical detection element in a state in which a phase pattern for compensating for the wavefront distortion is displayed in a specific target region among the N regions of the spatial light modulator; a second detecting step of detecting the light intensity distribution through the optical detection element in a state in which a spatially non-linear phase pattern is displayed in the specific target region before or after the first detecting step; and a first specifying step of specifying a converging spot corresponding to the specific target region among the M converging spots based on a change in the light intensity distribution between the first detecting step and the second detecting step.

The program for the adaptive optics system and the storage medium storing the program include the steps from the first detecting step to the first specifying step. Accordingly, it is possible to accurately specify the converging spot corresponding to the specific target region and improve the precision of wavefront distortion compensation. In addition, it is possible to prevent the number of components from increasing because it is unnecessary to add a new component such as an optical plate and maintain the precision of wavefront detection by suppressing an increase of loss of light to be measured.

Advantageous Effects of Invention

According to a correspondence relation specifying method for an adaptive optics system, an adaptive optics system, and a storage medium storing a program for an adaptive optics system according to an aspect of the present invention, it is possible to compensate for larger wavefront distortion by accurately specifying a correspondence relation between a converging spot of a wavefront sensor and a region on a modulation surface of a spatial light modulator to be controlled based on a position of the converging spot while an increase of the number of components and an increase of loss of light to be measured are suppressed.

BRIEF DESCRIPTION OF DRAWINGS

FIG. 9 is a diagram conceptually illustrating light intensity distribution data (Shack-Hartmann-Gram) detected by the image sensor of the wavefront sensor.

DESCRIPTION OF EMBODIMENTS

Hereinafter, embodiments of a correspondence relation specifying method for an adaptive optics system, an adaptive optics system, a program for an adaptive optics system, and a storage medium storing a program for an adaptive optics system according to an aspect of the present invention will be described with reference to the accompanying drawings. Also, the same elements are assigned the same reference signs in the description of the drawings and redundant description thereof will be omitted. Also, in the following description, it is assumed that a "phase distribution" indicates two-dimensionally distributed phase values, a "phase pattern" indicates a pattern obtained by coding the phase distribution (two-dimensional phase values) based on a certain standard, and a "phase profile" indicates a distribution of phase values in a certain direction (line) in the phase distribution.

Figure 1:
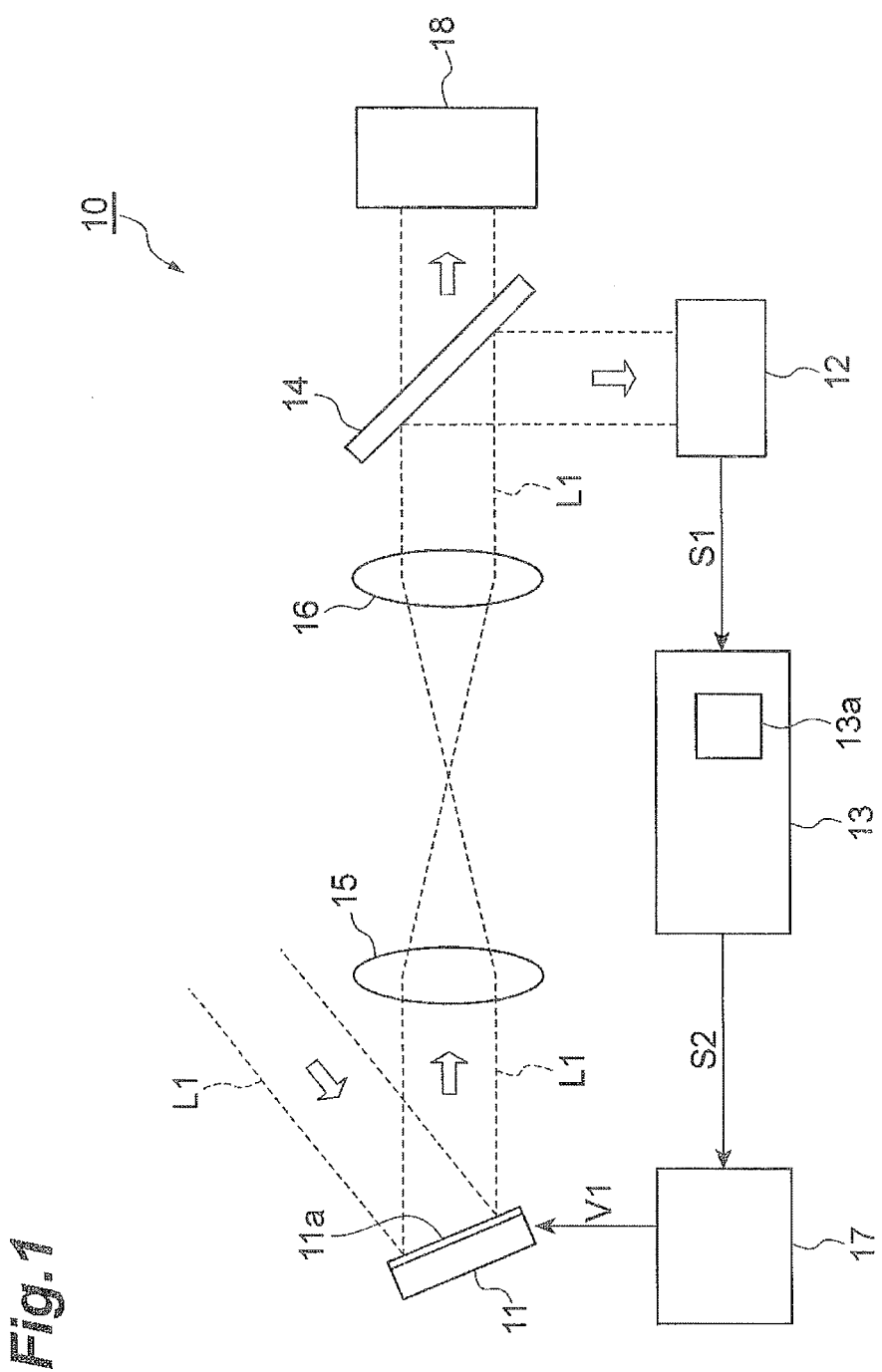
FIG. 1 is a diagram schematically illustrating a configuration of an adaptive optics system according to an embodiment.

FIG. 1 is a diagram schematically illustrating a configuration of an adaptive optics system 10 according to this embodiment. The adaptive optics system 10, for example, is embedded in an ophthalmologic inspection apparatus, a laser processing apparatus, a microscope apparatus, an adaptive optics apparatus, or the like. This adaptive optics system 10 includes a spatial light modulator (SLM) 11, a wavefront sensor 12, a control unit 13, a beam splitter 14, relay lenses 15 and 16, and a control circuit unit 17.

The spatial light modulator 11 receives an optical image L1 by a modulation surface 11a which displays a phase pattern and modulates a wavefront shape of the optical image L1 to output the modulated wavefront shape. The optical image L1 incident on the spatial light modulator 11, for example, is light emitted from a laser light source or a super luminescent diode (SLD) or reflected light, scattered light, fluorescent light, or the like generated from an observation object irradiated with light. The wavefront sensor 12 provides the control unit 13 with data S1 including information about the wavefront shape of the optical image L1 reaching from the spatial light modulator 11 (typically indicating distortion of a wavefront, that is, displacement of a wavefront from a reference wavefront, shown due to an aberration of an optical system). The control unit 13 generates a control signal S2 for displaying a phase pattern suitable for the spatial light modulator 11 based on the data S1 obtained from the wavefront sensor 12. In an example, the control unit 13 includes an input unit configured to input the data S1 from the wavefront sensor 12, an aberration calculation unit configured to calculate an aberration from the data S1, a phase pattern calculation unit configured to calculate a phase pattern to be displayed in the spatial light modulator 11, and a signal generation unit configured to generate the control signal S2 according to the calculated phase pattern. The control circuit unit 17 receives the control signal S2 from the control unit 13 and applies a voltage V1 based on the control signal S2 to a plurality of electrodes of the spatial light modulator 11.

The beam splitter 14 is arranged between the wavefront sensor 12 and the spatial light modulator 11 and branches the optical image L1. The beam splitter 14 may be a beam splitter of a polarization direction independent type, a polarization direction dependent type, or a wavelength dependent type (dichroic mirror). One optical image L1 branched by the beam splitter 14, for example, is sent to an optical detection element 18 such as a CCD, a photomultiplier tube, or an avalanche photodiode. The optical detection element 18, for example, is embedded in a scanning laser ophthalmoscope (SLO), an optical coherence tomography (OCT) camera, an ocular fundus camera, a microscope, a telescope, or the like. In addition, the other optical image L1 branched by the beam splitter 14 is incident on the wavefront sensor 12.

The relay lenses 15 and 16 are arranged side by side in an optical axis direction between the wavefront sensor 12 and the spatial light modulator 11. The wavefront sensor 12 and the spatial light modulator 11 are maintained in a mutually optical conjugate relation by the relay lenses 15 and 16. Also, an optical imaging lens and/or a polarization mirror, etc. may be further arranged between the wavefront sensor 12 and the spatial light modulator 11.

Figure 2:
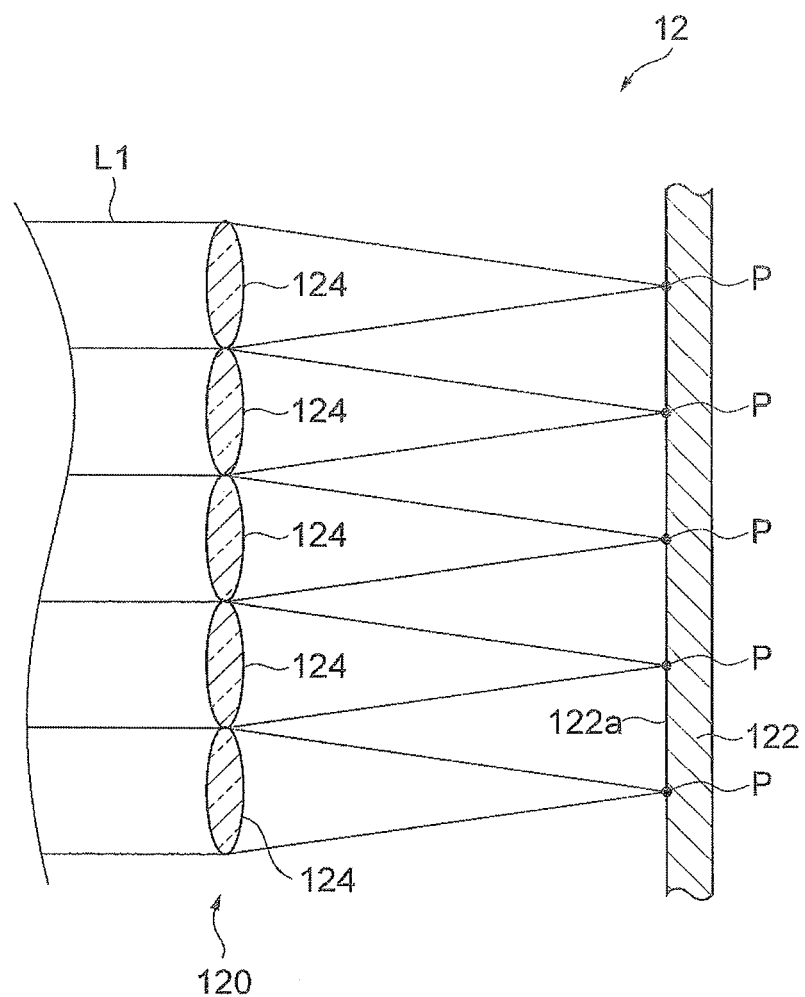
FIG. 2 is a cross-sectional view schematically illustrating a configuration of a wavefront sensor of an embodiment and illustrates a cross section along an optical axis of an optical image.
Figure 3:
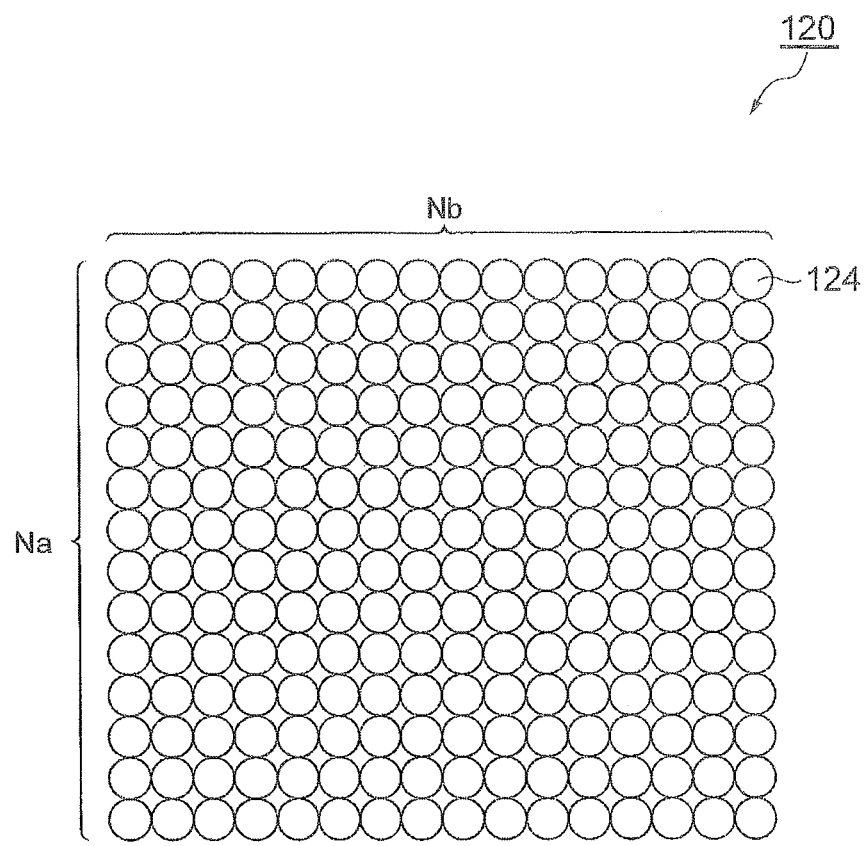
FIG. 3 is a view of a lens array provided in the wavefront sensor viewed in an optical axis direction of an optical image.

FIG. 2 is a cross-sectional view schematically illustrating a configuration of the wavefront sensor 12 of this embodiment and illustrates a cross section along the optical axis of the optical image L1. FIG. 3 is a view of a lens array 120 provided in the wavefront sensor 12 viewed in the optical axis direction of the optical image L1.

Although the wavefront sensor 12 may be of an interference type or a non-interference type, the non-interference type Shack-Hartmann wavefront sensor having the lens array 120 and the image sensor (optical detection element) 122 is used as the wavefront sensor 12 in this embodiment. When the non-interference type wavefront sensor 12 is used, there is an advantage in that vibration insensitivity is excellent and a configuration of the wavefront sensor and a process of calculating measurement data can be simpler than when the interference type wavefront sensor 12 is used.

As illustrated in FIG. 3, the lens array 120 has N (N is a natural number) lenses 124. The N lenses 124, for example, are arranged in a two-dimensional lattice shape of Na rows and Nb columns (Na and Nb are integers greater than or equal to 2).

Also, the image sensor 122 illustrated in FIG. 2 has a light receiving surface 122a at a position overlapping a rear focal plane of the N lenses 124 constituting the lens array 120 and detects a light intensity distribution including M converging spots P (M is a natural number and M≤N) formed by the N lenses 124. In general, because light radiated to the lens array 120 is input to some lenses 124 of the lens array 120, the converging spot P is formed by the lens 124 irradiated with input light. Accordingly, the number of lenses 124, N', located within an irradiation range of the input light among the N lenses 124 constituting the lens array 120 is equal to the number of converging spots P, M. Of course, when the entire lens array 120 is irradiated with the input light, the number N becomes equal to the number N' and N=M. In the control unit 13 to be described below, the wavefront shape of the optical image L1 (a distribution of phase gradients) is measured based on the light intensity distribution. That is, a magnitude of displacement between the position of the converging spot P by the lens 124 and the reference position is in proportion to a slope of a local wavefront of the optical image L1 incident on the lens 124. Therefore, it is possible to calculate the magnitude of the positional displacement of the converging spot P from the reference position for every lens 124 and measure the wavefront shape of the optical image L1 based on the positional displacement of the converging spot P.

Also, pixels constituting the light receiving surface 122a of the image sensor 122 are also arranged in a two-dimensional lattice shape and a horizontal direction and a vertical direction of the pixels match a horizontal direction and a vertical direction of the lens array 120, respectively. However, a pixel pitch of the image sensor 122 becomes sufficiently smaller than a pitch of the lens array 120 so that the magnitude of displacement of the converging image position from the reference position can be detected with high precision.

Also, it is possible to designate a position at which an optical axis of each of the plurality of lenses 124 intersects the light receiving surface 122a of the image sensor 122 as the reference position to be used to calculate the magnitude of the displacement of the converging image position. This position is easily obtained through center-of-gravity calculation using a converging image obtained by causing parallel plane waves to be perpendicularly incident on each lens 124.

The spatial light modulator 11 is an element which receives the optical image L1 from a light source or an observation object and modulates a wavefront of the optical image L1 to output the modulated wavefront. Specifically, the spatial light modulator 11 has a plurality of pixels (control points) arranged in a two-dimensional lattice shape and changes a modulation amount (for example, a phase modulation amount) of each pixel according to the control signal S2 provided from the control unit 13. The spatial light modulator 11, for example, includes a liquid crystal on silicon (LCOS) spatial light modulator, an electrical address type spatial light modulator formed by coupling an LCD element and an optical address type liquid-crystal spatial light modulator, or micro electro mechanical systems (MEMS). Also, although the reflection type spatial light modulator 11 is illustrated in FIG. 1, the spatial light modulator 11 may be of a transmission type.

Figure 4:
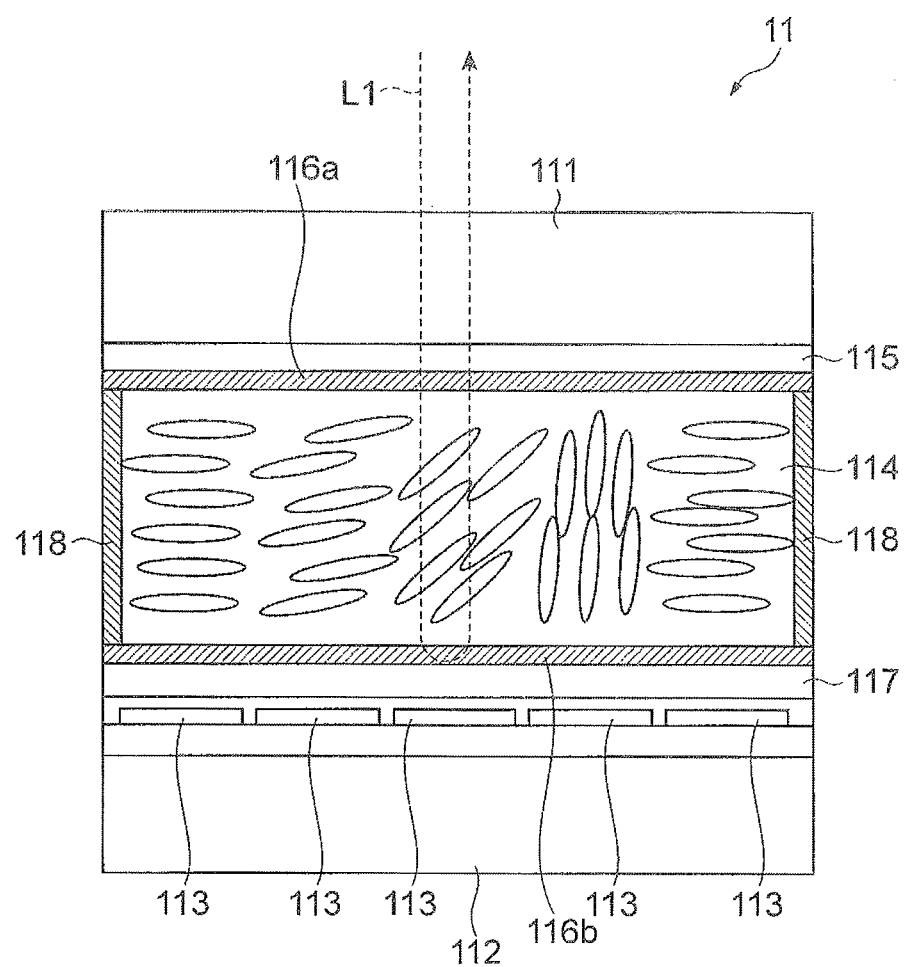
FIG. 4 is a cross-sectional view schematically illustrating an LCOS type spatial light modulator as an example of a spatial light modulator of an embodiment and illustrates a cross section along the optical axis of the optical image.

FIG. 4 is a cross-sectional view schematically illustrating an LCOS type spatial light modulator as an example of the spatial light modulator 11 of this embodiment and illustrates a cross section along the optical axis of the optical image L1. This spatial light modulator 11 includes a transparent substrate 111, a silicon substrate 112, a plurality of pixel electrodes 113, a liquid crystal unit (modulation unit) 114, a transparent electrode 115, oriented films 116a and 116b, a dielectric mirror 117, and a spacer 118.

The transparent substrate 111 is formed of a material which transmits the optical image L1 and arranged along a main surface of the silicon substrate 112. The plurality of pixel electrodes 113 are arranged in a two-dimensional lattice shape on the main surface of the silicon substrate 112 and constitute pixels of the spatial light modulator 11. The transparent electrode 115 is arranged on the surface of the transparent substrate 111 opposite to the plurality of pixel electrodes 113. The liquid crystal unit 114 is arranged between the plurality of pixel electrodes 113 and the transparent electrode 115. The oriented film 116a is arranged between the liquid crystal unit 114 and the transparent electrode 115 and the oriented film 116b is arranged between the liquid crystal unit 114 and the plurality of pixel electrodes 113. The dielectric mirror 117 is arranged between the oriented film 116b and the plurality of pixel electrodes 113. The dielectric mirror 117 reflects the optical image L1 incident from the transparent substrate 111 and transmitted through the liquid crystal unit 114 and causes the optical image L1 to be re-emitted from the transparent substrate 111.

Also, the spatial light modulator 11 further includes a pixel electrode circuit (active matrix drive circuit) 119 configured to control a voltage to be applied between the plurality of pixel electrodes 113 and the transparent electrode 115. When the voltage is applied from the pixel electrode circuit 119 to any pixel electrode 113, a refractive index of the liquid crystal unit 114 on the pixel electrode 113 changes according to a magnitude of an electric field generated between the pixel electrode 113 and the transparent electrode 115. Accordingly, an optical path length of the optical image L1 transmitted through a relevant part of the liquid crystal unit 114 changes and consequently a phase of the optical image L1 changes. By applying voltages of various magnitudes to the plurality of pixel electrodes 113, it is possible to electrically write a spatial distribution of a phase adjustment amount and implement various wavefront shapes if necessary.

Description will now return to FIG. 1. In this adaptive optics system 10, the optical image L1 from a light source or an observation object (not illustrated) is first incident on the spatial light modulator 11 as substantially parallel light. The optical image L1 modulated by the spatial light modulator 11 is incident on the beam splitter 14 via the relay lenses 15 and 16 and is branched into two optical images. One optical image L1 after the branching is incident on the wavefront sensor 12. The data S1 including the wavefront shape (for example, phase distribution) of the optical image L1 is generated in the wavefront sensor 12 and the data S1 is provided to the control unit 13. The control unit 13 calculates the wavefront shape (phase distribution) of the optical image L1 according to necessity based on the data S1 from the wavefront sensor 12 and outputs the control signal S2 including the phase pattern for appropriately compensating for wavefront distortion of the optical image L1 to the spatial light modulator 11. Thereafter, the non-distortion optical image L1 compensated for by the spatial light modulator 11 is branched by the beam splitter 14 and is incident on the optical detection element 18 via an optical system (not illustrated) and captured.

Figure 5:
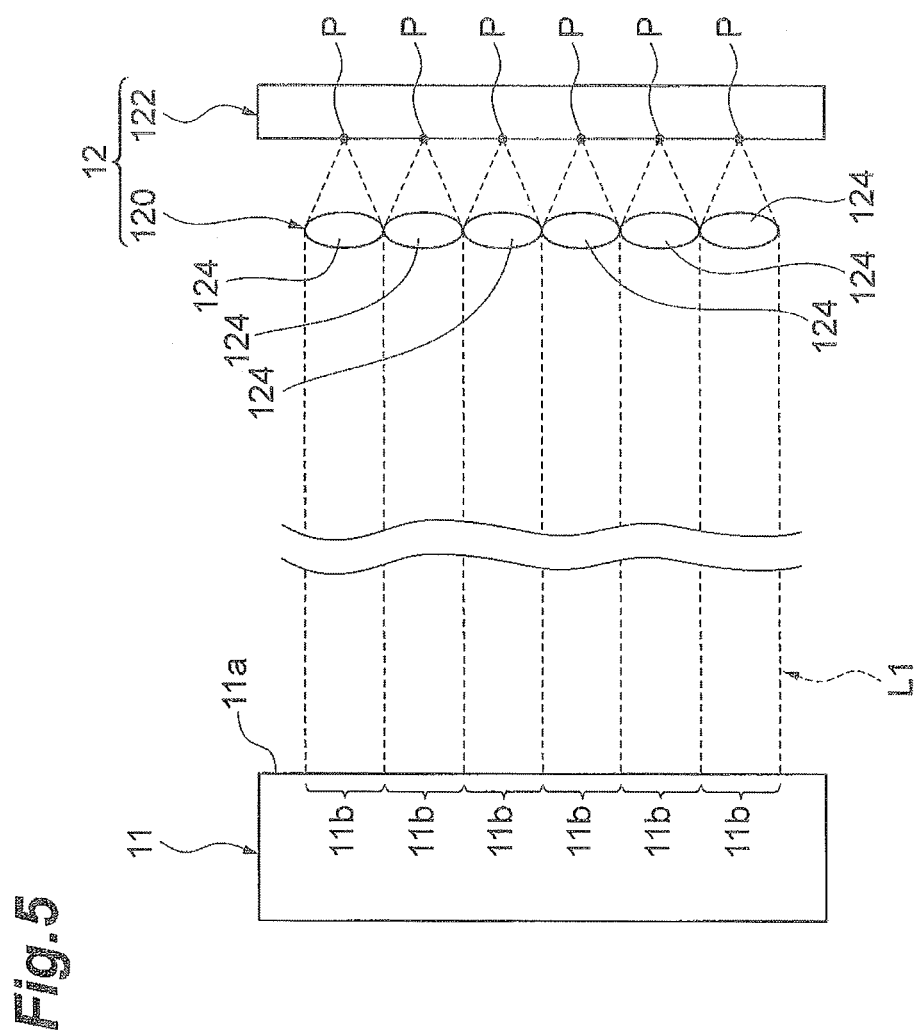
FIG. 5 is a diagram illustrating a simplified relation between the spatial light modulator and the wavefront sensor.

Here, FIG. 5 is a diagram illustrating a simplified relation between the spatial light modulator 11 and the wavefront sensor 12. In the adaptive optics system 10 including the above-described configuration, it is necessary to accurately specify a correspondence relation between M converging spots P formed by the N lenses 124 and N regions 11b on the modulation surface 11a of the spatial light modulator 11 to be controlled based on positional displacement information of the M converging spots P to accurately detect the wavefront shape of the optical image L1 in the wavefront sensor 12.

Figure 6:
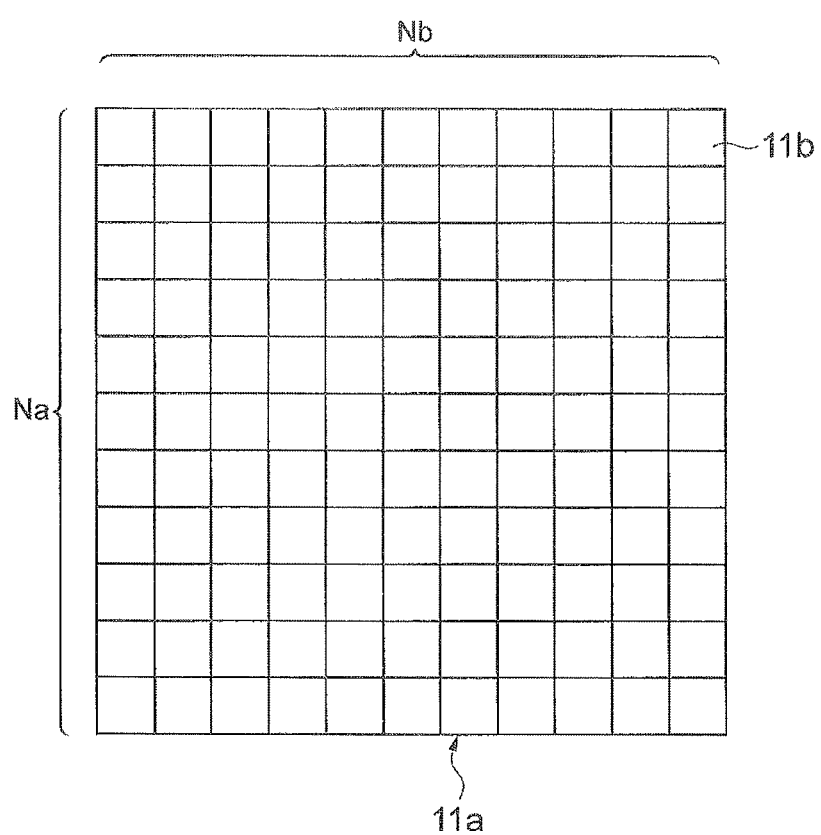
FIG. 6 is a front view of a modulation surface of the spatial light modulator.

FIG. 6 is a front view of the modulation surface 11a of the spatial light modulator 11. As illustrated in FIG. 6, the N regions 11b assumed on the modulation surface 11a are arranged in a two-dimensional shape (for example, Na rows and Nb columns) as in the N lenses 124, and correspond one-to-one to the N lenses 124. In addition, a plurality of pixels are included in each region 11b.

Hereinafter, a method of specifying the correspondence relation between the M converging spots P and the N regions 11b on the modulation surface 11a will be described in detail. Also, this specifying method, for example, is executed in the control unit 13 while a wavefront distortion compensation operation is executed. Specifically, this specifying method is stored as a program inside a storage region 13a of the control unit 13 illustrated in FIG. 1 and the control unit 13 performs the specifying method by reading the program.

Figure 7:
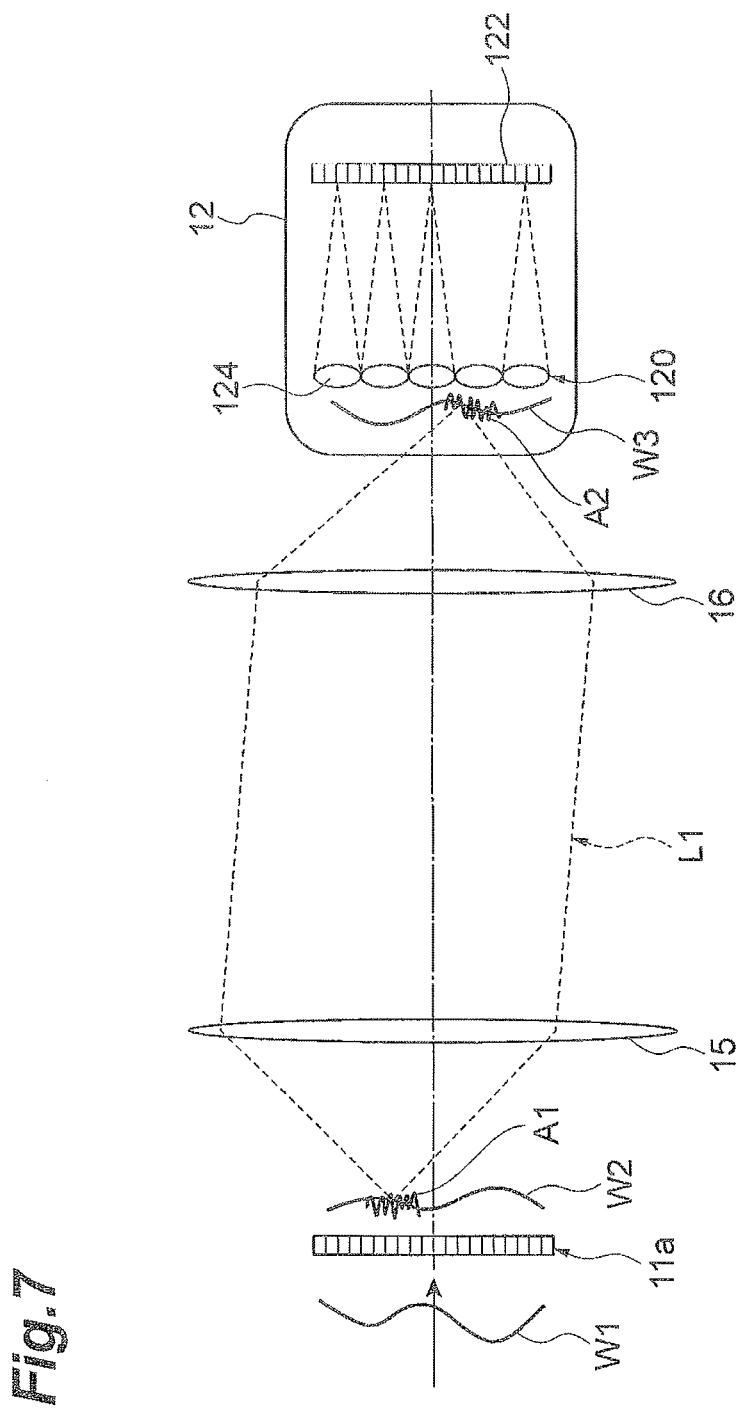
FIG. 7 is a conceptual diagram illustrating the principle of a method of specifying a corresponding relation between a region on the modulation surface and the converging spot.

FIG. 7 is a conceptual view illustrating the principle of the specifying method in this embodiment. In FIG. 7, the relay lenses 15 and 16, a wavefront W1 of an optical image incident on the modulation surface 11a, a wavefront W2 of the optical image emitted from the modulation surface 11a, and a wavefront W3 of the optical image incident on the wavefront sensor 12 are illustrated in addition to the modulation surface 11a of the spatial light modulator 11 and the wavefront sensor 12 (the lens array 120 and the image sensor 122). In addition, the optical image L1 emitted from the region 11b on the modulation surface 11a and reaching the lens 124 of the wavefront sensor 12 corresponding to the region 11b is illustrated in FIG. 7.

It is assumed that the wavefront distortion compensation operation is currently being executed and a phase pattern for compensating for the wavefront distortion is displayed in all the regions 11b on the modulation surface 11a. At this time, the wavefront W2 obtained by applying the wavefront according to the phase pattern to the incident wavefront W1 is emitted from the spatial light modulator 11 and the wavefront W3 via a conjugate optical system including the relay lenses 15 and 16 is incident on the wavefront sensor 12.

Here, the spatially non-linear phase pattern (for example, a random distribution in which a distribution of magnitudes of phases is irregular, a defocus distribution which increases a diameter of the converging spot, or the like) is displayed instead of the phase pattern for compensating for the wavefront distortion in a certain region 11b (hereinafter referred to as a specific target region) on the modulation surface 11a. Then, the wavefront of the part corresponding to the specific target region in the emission wavefront W2 is disturbed (part A1 of FIG. 7). The disturbance of the wavefront also occurs in a part incident on the lens 124 corresponding one-to-one to the specific target region in the incident wavefront W3 for the wavefront sensor 12 (part A2 of FIG. 7). Thereby, the converging spot P formed by the lens 124 diverges and the converging spot P is not formed, or its light intensity becomes weak.

Figure 8:
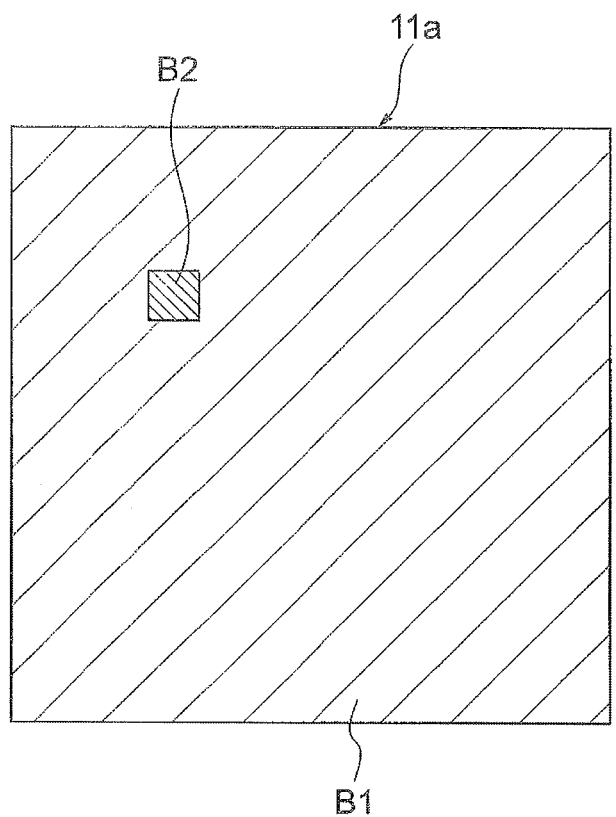
FIG. 8 is a diagram conceptually illustrating a phase pattern displayed on the modulation surface.

FIG. 8 is a diagram conceptually illustrating the phase pattern displayed on the modulation surface 11a. In FIG. 8, a region B1 is a region in which a phase pattern for compensating for the wavefront distortion is displayed and a region B2 is a region (that is, a specific target region) in which the spatially non-linear phase pattern is displayed. As described above, in this embodiment, the spatially non-linear phase pattern is displayed in one specific target region B2 of the N regions 11b.

FIG. 9 is a diagram conceptually illustrating light intensity distribution data (Shack-Hartmann-Gram) detected by the image sensor 122 of the wavefront sensor 12. FIG. 9(a) illustrates light intensity distribution data D1 of the case in which the phase pattern for compensating for the wavefront distortion is displayed in the N regions 11b of the modulation surface 11a and FIG. 9(b) illustrates light intensity distribution data D2 of the case in which the spatially non-linear phase pattern is displayed in one specific target region of the N regions 11b and the phase pattern for compensating for the wavefront distortion is displayed in another region.

As illustrated in FIG. 9(a), the M converging spots P corresponding to each region 11b are included in the light intensity distribution data when the phase pattern for compensating for the wavefront distortion is displayed in the N regions 11b. On the other hand, when the spatially non-linear phase pattern is displayed in one specific target region as illustrated in FIG. 9(b), converging spots P corresponding to (N−1) other regions are formed. However, the converging spot corresponding to the specific target region is not formed or its maximum intensity is reduced even when the converging spot is formed (part C in the drawing). Accordingly, it is possible to specify a converging spot P corresponding to a specific target region based on a change from the light intensity distribution data D1 illustrated in FIG. 9(a) to the light intensity distribution data D2 illustrated in FIG. 9(b).

Figure 10:
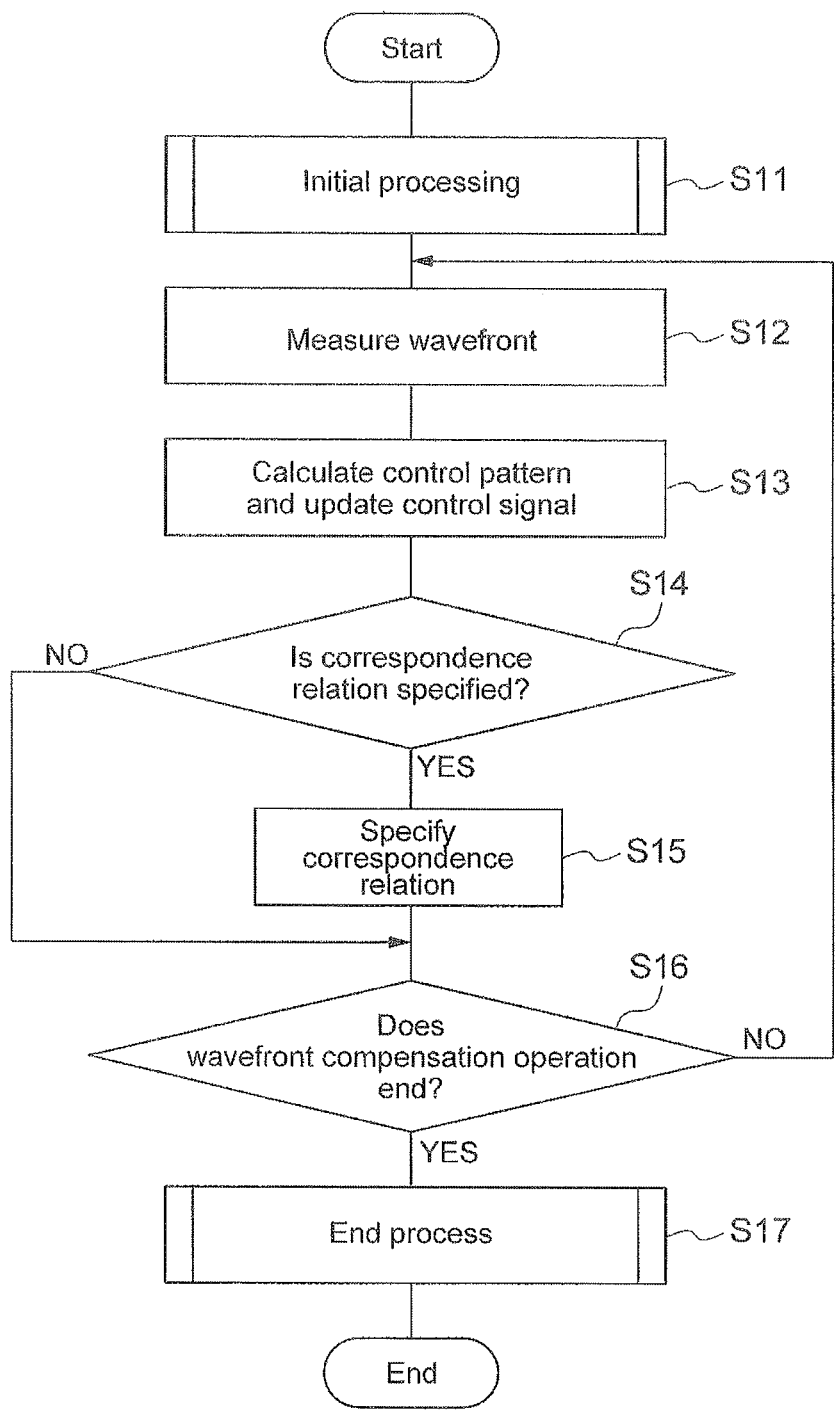
FIG. 10 is a flowchart illustrating an operation and a wavefront compensation method of an adaptive optics system of an embodiment.

An operation and wavefront compensation method of the adaptive optics system 10 including a method of specifying the correspondence relation between each region 11b of the modulation surface 11a and the converging spot P described above will be described with reference to FIG. 10. FIG. 10 is a flowchart illustrating the operation and wavefront compensation method of the adaptive optics system 10 of this embodiment. Also, a program stored inside the storage region 13a of the control unit 13 is a program for the adaptive optics system for causing the control unit 13 to execute the following method. Also, the control unit 13 can be mainly constituted of a computer including a CPU, a RAM and a ROM which are main storage apparatuses, a communication module for performing communication, and hardware resources such as an auxiliary storage apparatus such as a hard disk. The program for the adaptive optics system is stored in a storage medium inserted into the computer and accessed or a storage medium provided in the computer. This storage medium, for example, corresponds to a magnetic disc, an optical disc, a CD-ROM, a USB memory, a memory (the storage region 13a) embedded in the computer, or the like.

In the adaptive optics system 10, initial processing of the control unit 13 is first performed (step S11). In this initial processing step S11, for example, securement of a memory region necessary for a calculation process, initial setting of parameters, etc. are performed.

Figure 11:
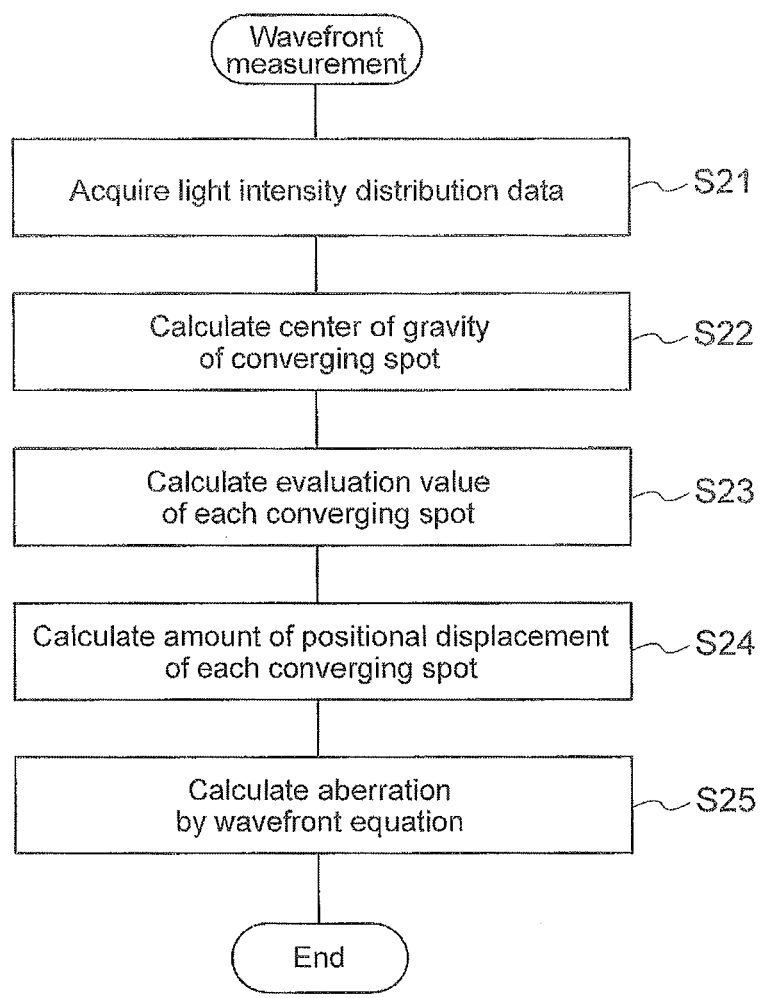
FIG. 11 is a flowchart illustrating an example of a wavefront measuring process to be executed in a control unit.

Next, the wavefront measurement (aberration measurement) is performed (step S12). In this wavefront measuring step S12, the control unit 13 obtains a wavefront shape based on the light intensity distribution data acquired by the wavefront sensor 12. Here, FIG. 11 is a flowchart illustrating an example of a wavefront measuring process to be executed in the control unit 13. As illustrated in FIG. 11, the control unit 13 first acquires light intensity distribution data created by the image sensor 122 of the wavefront sensor 12 (step S21, first detecting step in this embodiment). As illustrated in FIG. 9(a), the light intensity distribution data includes the M converging spots P formed by the N lenses 124. Next, the control unit 13 specifies position coordinates of each of the M converging spots by calculating the center of gravity (primary moment of light intensity) of each of the M converging spots P included in the light intensity distribution data (step S22). When the center of gravity is calculated, the exclusion of a data value less than a predetermined threshold value, a noise reduction process, etc. may also be performed. Subsequently, evaluation values of the M converging spots P are calculated (step S23). The evaluation value, for example, is a numeric value representing the reliability of each converging spot P such as a maximum light intensity or a spot diameter (spread condition) of each converging spot P, a high-order moment of light intensity, a minimum light intensity within a spot diameter, or a sum of light intensities within the spot diameter. In the subsequent step, only information related to the converging spot P for which the evaluation value satisfies a predetermined condition is used in calculation. Subsequently, a distance (an amount of positional displacement) between the position coordinates of each converging spot P and the reference position is calculated for every converging spot P (step S24). Thereafter, the wavefront distortion (aberration) is calculated by applying the amount of positional displacement calculated in step S24 to a wavefront equation (step S25).

Description will now return to FIG. 10. Subsequently, the control unit 13 calculates a phase pattern (control pattern) for compensating for wavefront distortion to be displayed on the modulation surface 11a of the spatial light modulator 11 (step S13). In step S13, for example, a phase pattern for causing wavefront distortion (aberration) calculated in a previous wavefront measuring step S12 to be close to zero is calculated based on an algorithm of negative feedback control. A control signal S2 according to the calculated phase pattern is output from the control unit 13 to the control circuit unit 17. The control circuit unit 17 supplies a control voltage V1 according to the control signal S2 to the spatial light modulator 11.

Figure 12:
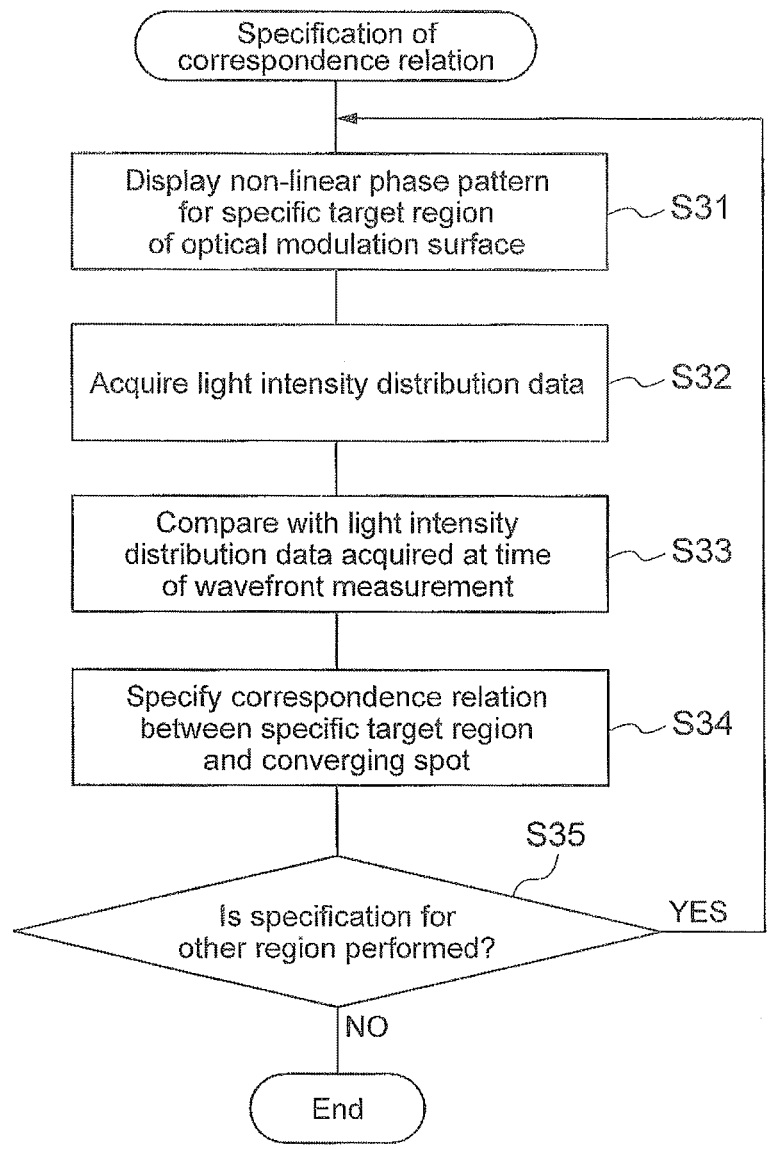
FIG. 12 is a flowchart illustrating an example of a method of specifying the converging spot and the region on the modulation surface in a correspondence relation specifying step.

Subsequently, the control unit 13 determines whether a correspondence relation between each region 11b of the modulation surface 11a and the converging spot P is specified (step S14). When this correspondence relation is specified (step S14; Yes), the control unit 13 performs a process illustrated in FIG. 12 (step S15, correspondence relation specifying step). FIG. 12 is a flowchart illustrating an example of a method of specifying the correspondence relation between the converging spot P and the region 11b on the modulation surface 11a in the correspondence relation specifying step S15.

As illustrated in FIG. 12, the control unit 13 first displays the spatially non-linear phase pattern instead of the phase pattern for compensating for the wavefront distortion in a certain specific target region on the modulation surface 11a as illustrated in FIG. 8 (step S31). Next, the control unit 13 acquires light intensity distribution data created by the image sensor 122 of the wavefront sensor 12 in a state in which the spatially non-linear phase pattern is displayed in the specific target region (step S32, second detection step in this embodiment). When the converging spot corresponding to the specific target region is not formed as illustrated in FIG. 9(b), (M−1) converging spots P formed by (N−1) lenses 124 are included in the light intensity distribution data. Also, even when the converging spot corresponding to the specific target region is formed in a weak intensity, the number of converging spots P included in the light intensity distribution data becomes M if the evaluation value calculated in step S23 is sufficiently large. Subsequently, the control unit 13 compares the light intensity distribution data (for example, FIG. 9(a)) acquired in the first detecting step S21 with the light intensity distribution data (for example, FIG. 9(b)) acquired in the second detecting step S32 (step S33). In this comparison, for example, it is only necessary to calculate a difference or ratio between the light intensity distribution data (for example, FIG. 9(a)) acquired in the first detecting step S21 and the light intensity distribution data (for example, FIG. 9(b)) acquired in the second detecting step S32. Alternatively, the center-of-gravity calculation as in step S23 is performed on the light intensity distribution data and a feature quantity such as a center of gravity of the converging spot calculated by the center-of-gravity calculation, a spot diameter, or a sum of light intensities within the spot diameter may be used. Also, because light intensity distribution data is acquired in a state in which a phase pattern for compensating for the wavefront distortion is displayed in all of the N regions 11b including the specific target region in the first detecting step S21, the light intensity distribution data includes the converging spot P corresponding to the specific target region. The converging spot P in which the light intensity or the feature quantity of the light intensity distribution data significantly changes is specified in the comparison, and it is determined that the specified converging spot P is a converging spot corresponding to the specific target region (step S34, first specifying step in this embodiment). Thereafter, the control unit 13 determines whether it is necessary to specify the correspondence relation with the converging spot in still another region on the modulation surface 11a (step S35). When the specification is necessary (step S35; Yes), the control unit 13 iterates the above-described steps S31 to S34 for another region. In addition, when the specification is unnecessary (step S35; No), the control unit 13 ends the process.

Description will now return to FIG. 10. The control unit 13 externally receives a command signal indicating whether to end the wavefront compensation operation after the correspondence relation between the converging spot P and the region 11b is specified in the correspondence relation specifying step S15 or when it is determined that it is unnecessary to specify the correspondence relation between the converging spot P and the region 11b (step S16). This command signal, for example, is input by a person who manipulates an apparatus including the adaptive optics system 10. When there is an end command (step S16; Yes), the process ends via an end processing step S17. In addition, when there is no end command (step S16; No), the above-described steps S12 to S16 are iterated. Also, in the end processing step S17, for example, release or the like of a memory region of the control unit 13 is performed.

Effects obtained by the adaptive optics system 10 of this embodiment, the correspondence relation specifying method therefor, the program for the adaptive optics system, and the storage medium storing the program for the adaptive optics system described above will be described.

In this embodiment, in the first detecting step S21, the light intensity distribution is detected in the image sensor 122 of the wavefront sensor 12 in a state in which the phase pattern for compensating for the wavefront distortion is displayed in the specific target region of the spatial light modulator 11. In the first detecting step S21, the converging step P corresponding to the specific target region is formed at any position on the image sensor 122. In addition, as the second detecting step S32, the light intensity distribution is detected in the image sensor 122 of the wavefront sensor 12 in a state in which the spatially non-linear phase pattern is displayed in the above-described specific target region. In this second detecting step S32, light diverges according to the non-linear phase pattern displayed in the specific target region and the converging spot P corresponding to the specific target region is not formed or its light intensity is weakened.

Thereafter, when the light intensity distributions obtained in the first detecting step S21 and the second detecting step S32 are compared with each other in the first specifying step S34, there is a clear converging spot P corresponding to the specific target region in the light intensity distribution obtained in the first detecting step S21, but there is no converging spot P corresponding to the specific target region in the light intensity distribution obtained in the second detecting step S32 or the clarity of the converging spot P is significantly degraded as compared with the first detecting step S21. Therefore, it is possible to accurately specify the converging spot P corresponding to the specific target region based on a change in a light intensity distribution between the first detecting step S21 and the second detecting step S32.

As described above, according to the adaptive optics system 10 of this embodiment, the correspondence relation specifying method therefor, the program for the adaptive optics system, and the storage medium storing the program for the adaptive optics system, it is possible to accurately specify a correspondence relation between the converging spot P of the wavefront sensor 12 and the region 11b on the modulation surface 11a of the spatial light modulator 11 to be controlled based on the aberration calculated from the position of the converging spot P while the wavefront compensation operation is executed. Accordingly, it is possible to precisely compensate for larger wavefront distortion while continuing an operation of an apparatus in which the adaptive optics system 10 is embedded. In addition, it is possible to suppress an increase of the number of components because it is unnecessary to add a new component such as an optical plate as in the configuration disclosed in Patent Literature 1 and maintain wavefront detection precision by suppressing an increase of loss of an optical image L1.

Here, an example of a "spatially non-linear second phase pattern" displayed on the modulation surface 11a in step S31 is shown. FIGS. 13 to 16 are diagrams illustrating examples of such a phase pattern, wherein a magnitude of a phase is shown according to light and shade, a phase of a darkest part is 0 (rad), and a phase of a brightest part is $2\pi$ (rad).

Figure 13:
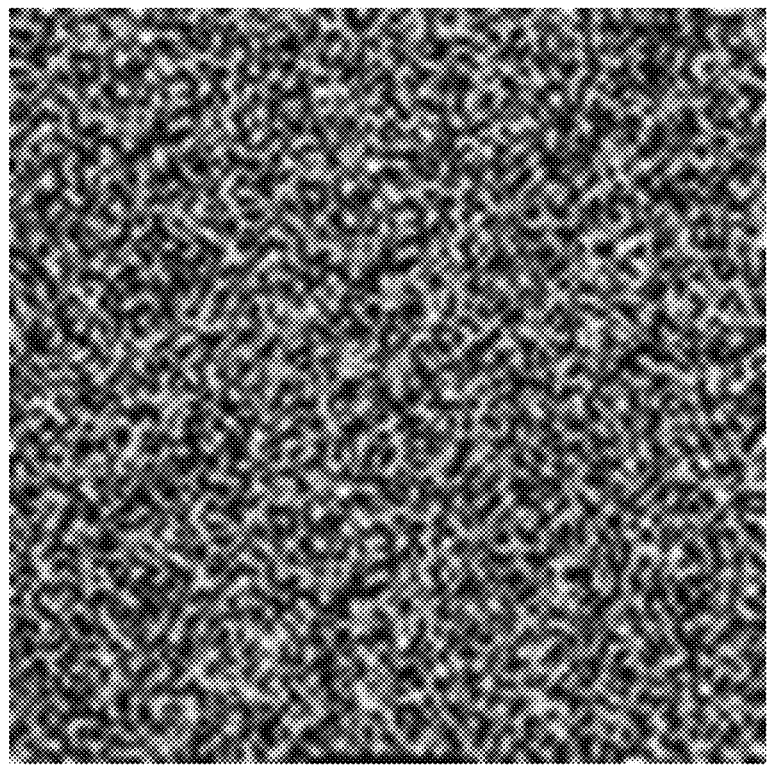
FIG. 13 is a diagram illustrating a random distribution in which a distribution of magnitudes of phases is irregular as an example of a spatially non-linear phase pattern.
Figure 14:
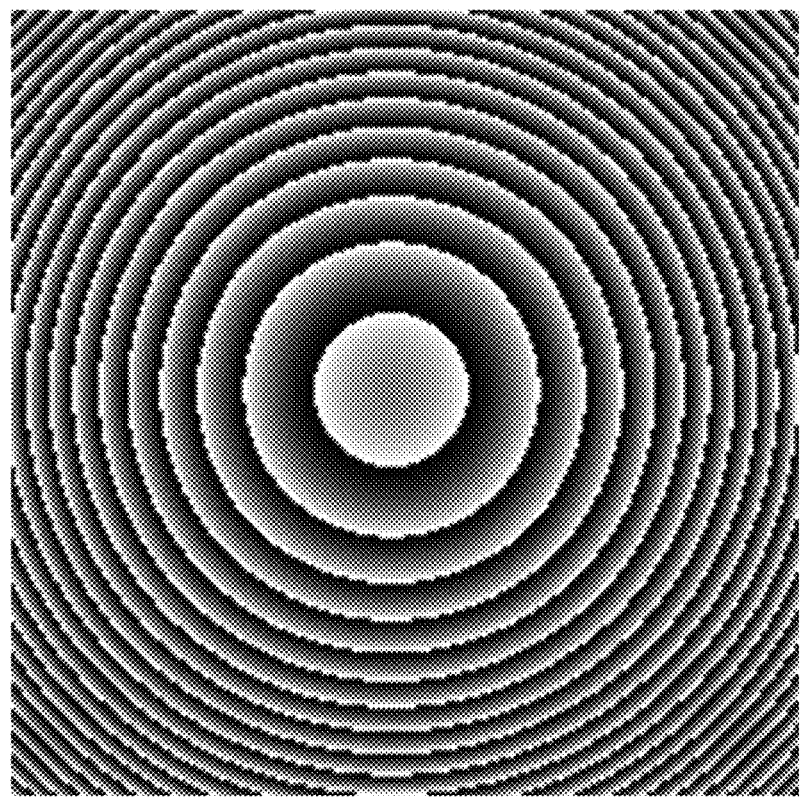
FIG. 14 is a diagram illustrating a defocus distribution which increases a diameter of a converging spot as an example of the spatially non-linear phase pattern.
Figure 15:
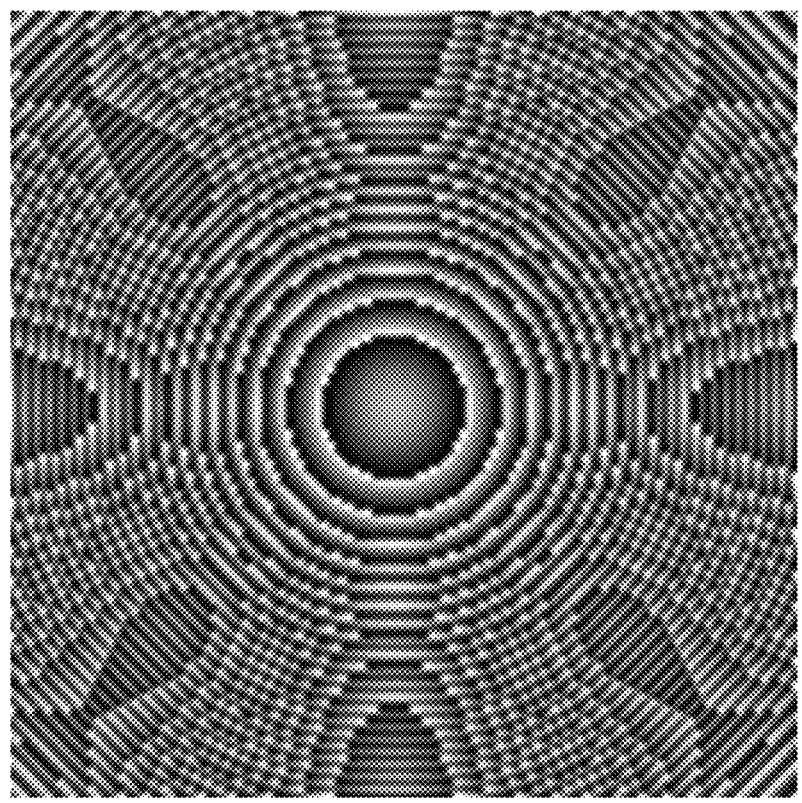
FIG. 15 is a diagram illustrating a distribution which causes a large spherical aberration in an optical image as an example of the spatially non-linear phase pattern.
Figure 16:
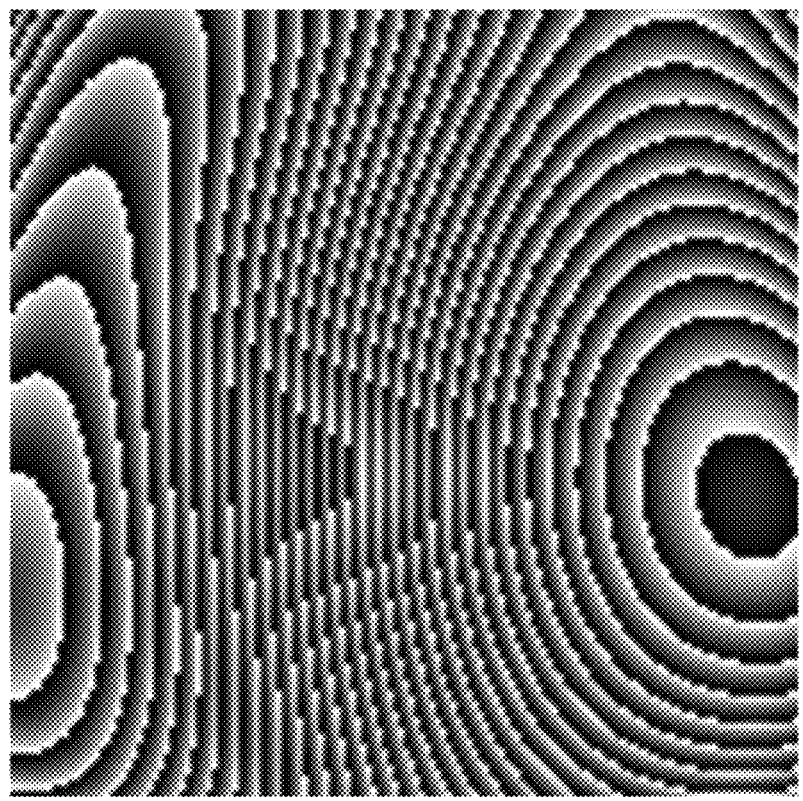
FIG. 16 is a diagram illustrating a distribution which causes a large high-order aberration in the optical image as an example of the spatially non-linear phase pattern.

FIG. 13 illustrates a random distribution in which a distribution of magnitudes of phases is irregular. When this phase pattern is displayed in the specific target region, the optical image L1 of a relevant part diverges and a clear converging spot P is not formed or a maximum light intensity is reduced. FIG. 14 illustrates a defocus distribution which increases a diameter of a converging spot P. When such a phase pattern is displayed in the specific target region, a clear converging spot P is not formed or the maximum light intensity is reduced because the optical image L1 of the relevant part is conversely widened without converging. Also, FIG. 15 illustrates a distribution which causes a large spherical aberration in the optical image L1. Instead of the phase pattern which causes the spherical aberration, a phase pattern which causes a large astigmatic aberration or coma aberration may be used. FIG. 16 illustrates a distribution in which an aberration including a higher-order aberration than a spherical aberration, an astigmatic aberration, or a coma aberration occurs in the optical image L1. Even when the phase pattern illustrated in FIG. 15 or 16 is displayed in the specific target region, the clear converging spot P is not formed. The spatially non-linear phase pattern may include at least one of the above-described distributions, may include a composite pattern in which at least one of the above-described distributions and a linear phase pattern are superimposed, or may include a composite pattern in which at least one of the above-described distributions and a phase pattern for compensating for wavefront distortion for which wavefront measurement is performed are superimposed.

In addition, a form in which a plurality of regular hexagonal pixels are arranged without gaps may be used as the spatial light modulator. In addition, the spatial light modulator using liquid crystal is described as an example in the above-described embodiments, but a spatial light modulator using a material having an electro-optic effect other than the liquid crystal, a spatial light modulator in which a pixel is formed of a micro-mirror, a variable mirror for deforming a film mirror using an actuator, or the like may be used.

Although the second detecting step S32 is performed after the first detecting step S21 in this embodiment, the order may be reversed. That is, after the spatially non-linear phase pattern is first displayed in the specific target region and the image sensor 122 detects the light intensity distribution in such a state, the phase pattern for compensating for the wavefront distortion may be displayed in the specific target region and the light intensity distribution may be detected by the image sensor 122 in such a state. Even in this form, it is possible to similarly obtain the above-described effects.

First Modified Example

In the above-described embodiment, the light intensity distribution (FIG. 9(*a*)) including all of the M converging spots P is compared with the light intensity distribution (FIG. 9(*b*)) in which the converging spot P corresponding to the specific target region is not formed in step S33 within the correspondence relation specifying step S15. However, in step S33, it is only necessary to compare the light intensity distribution in which the converging spot P corresponding to the specific target region is formed with the light intensity distribution in which the converging spot P is not formed. Accordingly, for example, when steps S31 to S34 for a plurality of specific target regions are iterated, the light intensity distribution previously acquired in step S32 may be used as a comparison target.

Figure 17:
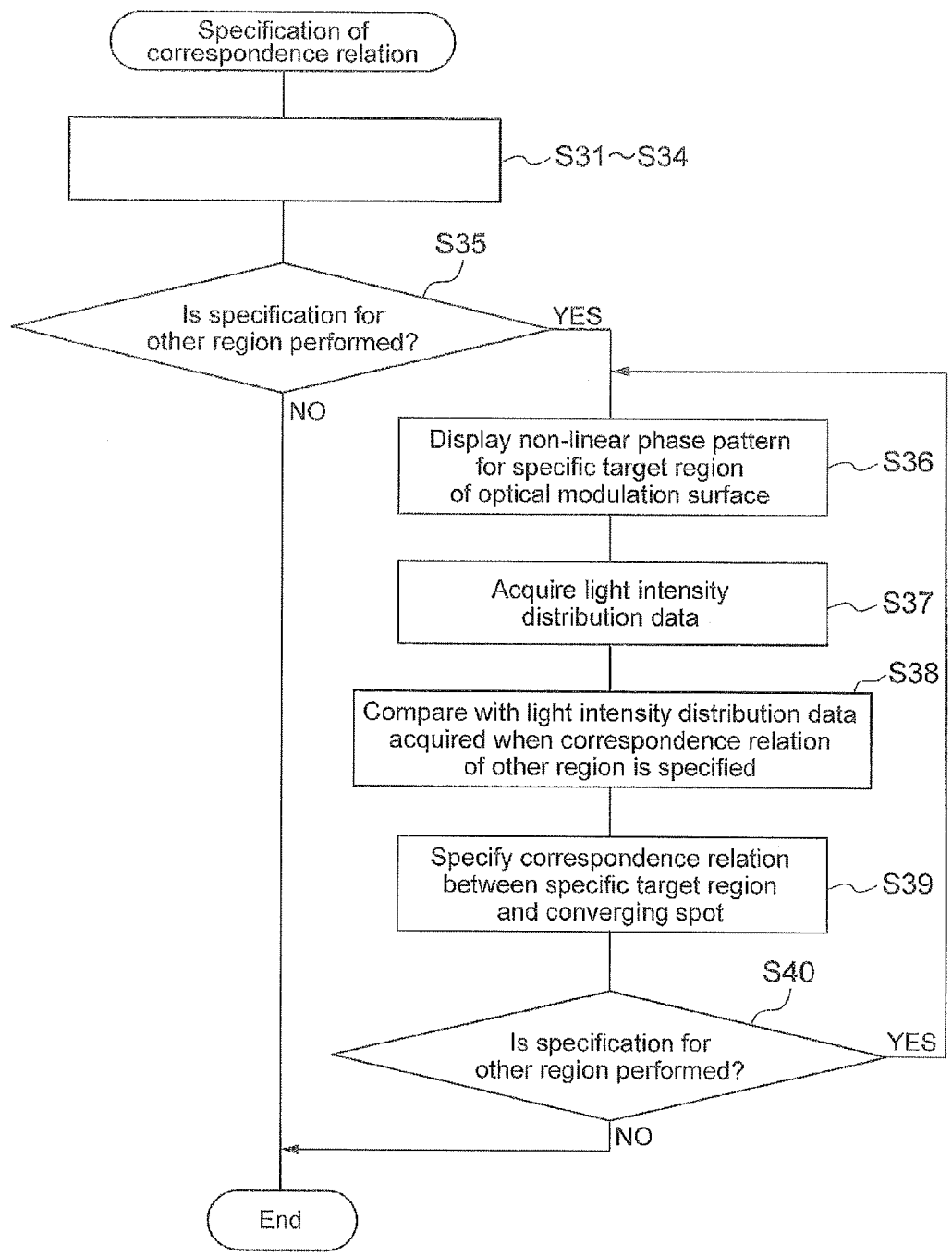
FIG. 17 is a flowchart illustrating an operation and a correspondence relation specifying method of a control unit of an adaptive optics system according to a first modified example.

FIG. 17 is a flowchart illustrating an operation and a correspondence relation specifying method of the control unit 13 of the adaptive optics system 10 according to this modified example. A difference of the flowchart illustrated in FIG. 17 from FIG. 12 is that steps S36 to S40 are provided as a branch from step S35. That is, when the correspondence relation for another region is specified after steps S31 to S34 are first executed in this modified example (step S35; Yes), steps S36 to S40 are executed.

In step S36, the control unit 13 causes the spatially non-linear phase pattern to be displayed in a specific target region separate from the specific target region selected in step S31 instead of a phase pattern for compensating for wavefront distortion. Simultaneously, the control unit 13 causes the phase pattern for compensating for the wavefront distortion to be displayed in another region 11*b* including the specific target region selected in step S31 instead of the spatially non-linear phase pattern.

Next, in step S37, the control unit 13 acquires light intensity distribution data created by the image sensor 122 of the wavefront sensor 12 in a state in which the above-described phase pattern is displayed (third detecting step in this modified example). The control unit 13 compares the light intensity distribution data acquired in the third detecting step S37 with the light intensity distribution data acquired in the second detecting step S32 (step S38). The control unit 13 specifies the converging spot P in which the light intensity or the spot diameter significantly changes in the comparison, and determines that the converging spot P is a converging spot corresponding to the above-described other specific target region (step S39, second specifying step in this embodiment). Thereafter, the control unit 13 determines whether it is necessary to specify a correspondence relation with a converging spot for still another specific target region on the modulation surface 11*a* (step S40). When the specification is necessary (step S40; Yes), the control unit 13 iterates the above-described steps S36 to S39 in still another specific target region. Also, when steps S36 to S39 are iterated, the light intensity distribution data obtained in step S37 with respect to a specified specific target region may be compared with the light intensity distribution data obtained in step S37 with respect to a specific target region intended to be specified in step S38. Also, when the specification is unnecessary (step S40: No), the control unit 13 ends the process.

In this modified example, the third detecting step S37 and the second specifying step S38 are further provided in addition to the correspondence relation specifying method of the above-described embodiment. Thereby, it is possible to efficiently specify the correspondence relation between each region 11*b* and the converging spot P while sequentially displaying the spatially non-linear phase pattern in the plurality of regions 11*b* of the spatial light modulator 11.

Second Modified Example

In the wavefront measuring step S12 of the above-described embodiment, light intensity distribution data (FIG. 9(*a*)) including all M converging spots P is acquired in step S21 and the wavefront shape is measured using the light intensity distribution data (steps S22 to S25). However, when the correspondence relation specifying step S15 has already been performed once or more, the light intensity distribution data acquired in the second detecting step S32 of the correspondence relation specifying step S15 may be used in the wavefront measuring step S12 and the wavefront shape may be measured. According to this method, it is possible to omit step S21 of the wavefront measuring step S12.

Figure 18:
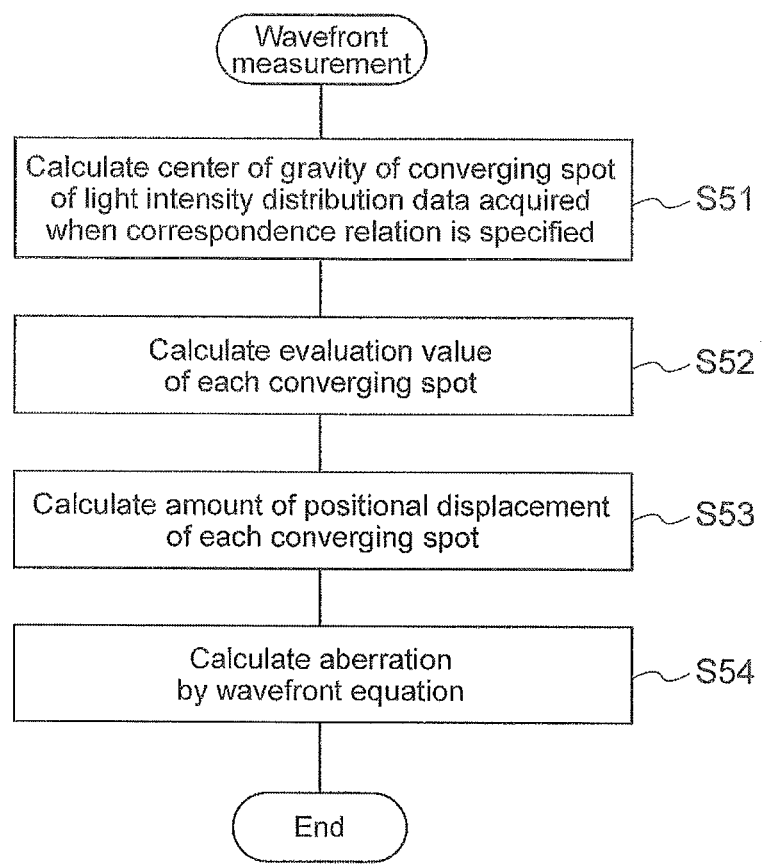
FIG. 18 is a flowchart illustrating a wavefront measuring step according to a second modified example.

FIG. 18 is a flowchart illustrating a wavefront measuring step according to this modified example. The control unit 13, for example, specifies position coordinates of each of N or fewer converging spots P by calculating a center of gravity of each of (M−1) converging spots P included in the light intensity distribution data (for example, see FIG. 9(b)) acquired in the second detecting step S32 of the already executed correspondence relation specifying step S15 (step S51). Subsequently, evaluation values of the N or less converging spots P are calculated (step S52) and a distance (an amount of positional displacement) between the position coordinates of each converging spot P and the reference position is calculated for each converging spot P (step S53). Also, details of steps S52 and S53 are similar to the above-described embodiments. Thereafter, the wavefront distortion (aberration) is calculated by applying the amount of positional displacement of each converging spot P calculated in step S53 to a wavefront equation (step S54).

In this modified example, the wavefront distortion is compensated for based on the wavefront shape obtained from the light intensity distribution data detected in the second detecting step S32. That is, in the method of this modified example, the wavefront distortion is compensated for based on the measured wavefront shape in a state in which the spatially non-linear phase pattern is displayed in the specific target region. In this case, the phase pattern for compensating for the wavefront distortion is not displayed in the specific target region, but it is possible to suppress an influence by the specific target region and sufficiently compensate for the wavefront distortion by limiting the specific target region to a small number of parts among the N regions 11b of the spatial light modulator 11. In addition, when the phase pattern displayed in the spatial light modulator 11 is calculated in this modified example, the phase pattern obtained by excluding a part corresponding to the specific target region from the measured wavefront shapes may be used. Alternatively, the entire phase pattern may be configured by combining the measured wavefront shape with the spatially non-linear phase pattern in the specific target region of the spatial light modulator 11 using all the calculated wavefront shapes.

Figure 19:
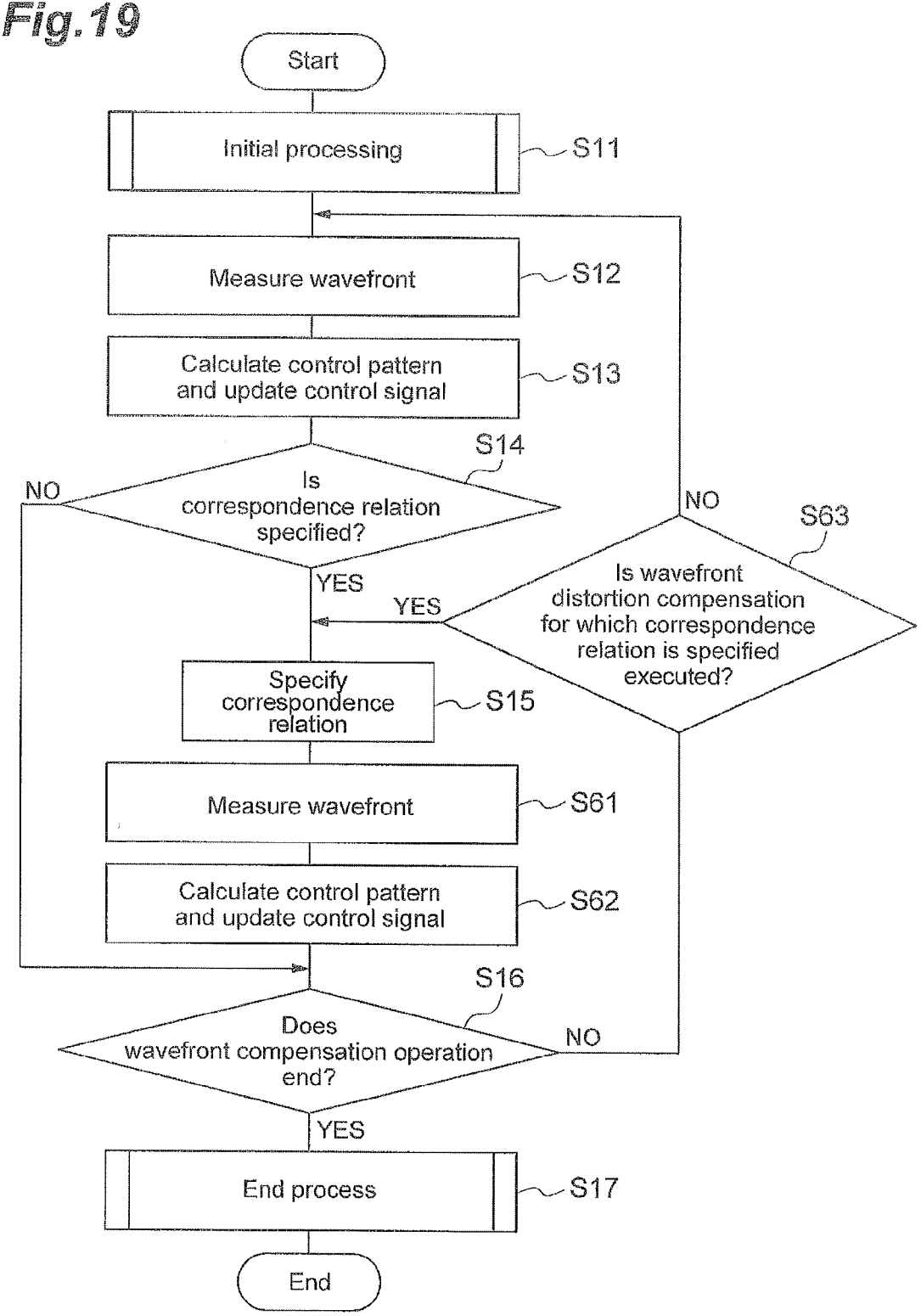
FIG. 19 is a flowchart illustrating an operation and a wavefront compensation method of the adaptive optics system.

In addition, in the above-described embodiment, the wavefront measuring step illustrated in FIG. 18 may be performed again after the specification (step S15) of the correspondence relation separate from the wavefront measuring step S12. FIG. 19 is a flowchart illustrating an operation and a wavefront compensation method of the adaptive optics system 10 of such a case.

In the method illustrated in FIG. 19, as in the above-described embodiment, the initial processing (step S11), the wavefront measurement (step S12), and the calculation (step S13) of the phase pattern for compensating for the wavefront distortion are first performed. Subsequently, the control unit 13 determines whether the correspondence relation between each region 11b of the modulation surface 11a and the converging spot P is specified (step S14). When the correspondence relation is specified (step S14; Yes), the control unit 13 performs a second wavefront measuring step S61 including steps S51 to S54 illustrated in FIG. 18 after the correspondence relation specifying step S15 (see FIG. 12) is performed. The calculation of the phase pattern for compensating for the wavefront distortion is performed again based on the wavefront distortion measured in the second wavefront measuring step S61 (step S62).

After the phase pattern for compensating for the wavefront distortion is calculated in step S62 or when it is determined that it is unnecessary to specify the correspondence relation between the converging spot P and the region 11b in step S14, the control unit 13 externally receives a command signal indicating whether to end the wavefront compensation operation (step S16). This command signal, for example, is input by a person who manipulates the apparatus including the adaptive optics system 10. When there is an end command (step S16; Yes), the process ends via the end processing step S17. In addition, when there is no end command (step S16; No), it is selected whether to execute wavefront distortion compensation for which the correspondence relation is specified (step S63). When the wavefront distortion compensation is not executed (step S63; No), the process proceeds to the above-described step S12. When the wavefront distortion compensation is executed (step S63; Yes), the process proceeds to the above-described step S15.

Third Modified Example

Figure 20:
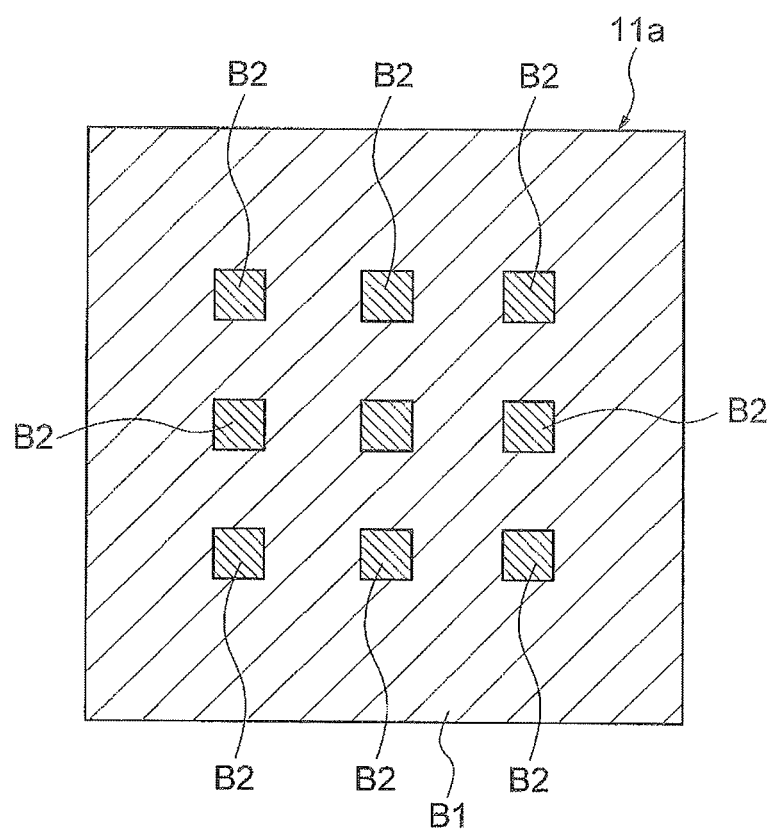
FIG. 20 is a diagram illustrating an example in which a plurality of specific target regions are set at one time.

One specific target region B2 is set in the modulation surface 11a as illustrated in FIG. 8 in the above-described embodiment, but a plurality of specific target regions B2 may be set at one time. FIG. 20 is a diagram illustrating an example in which a plurality of specific target regions are set at one time. In FIG. 20, the region B1 is a region in which the phase pattern for compensating for the wavefront distortion is displayed. As illustrated in FIG. 20, in this modified example, a plurality of regions 11b that are not adjacent to one another are set in the specific target region B2 and the spatially non-linear phase pattern is displayed.

According this modified example, a time required to specify the correspondence relation can be shortened because it is possible to specify a correspondence relation between a plurality of specific target regions B2 of the spatial light modulator 11 and a plurality of converging spots P at one time. Also, intervals between a plurality of specific target regions B2 may be set to be longer when an aberration of the optical image L1 is larger. In addition, when the wavefront shape is measured using the light intensity distribution data acquired in the correspondence relation specifying step S15 as in the second modified example, the measurement precision of the wavefront shape is further improved when the number of specific target regions B2 is smaller.

Figure 21:
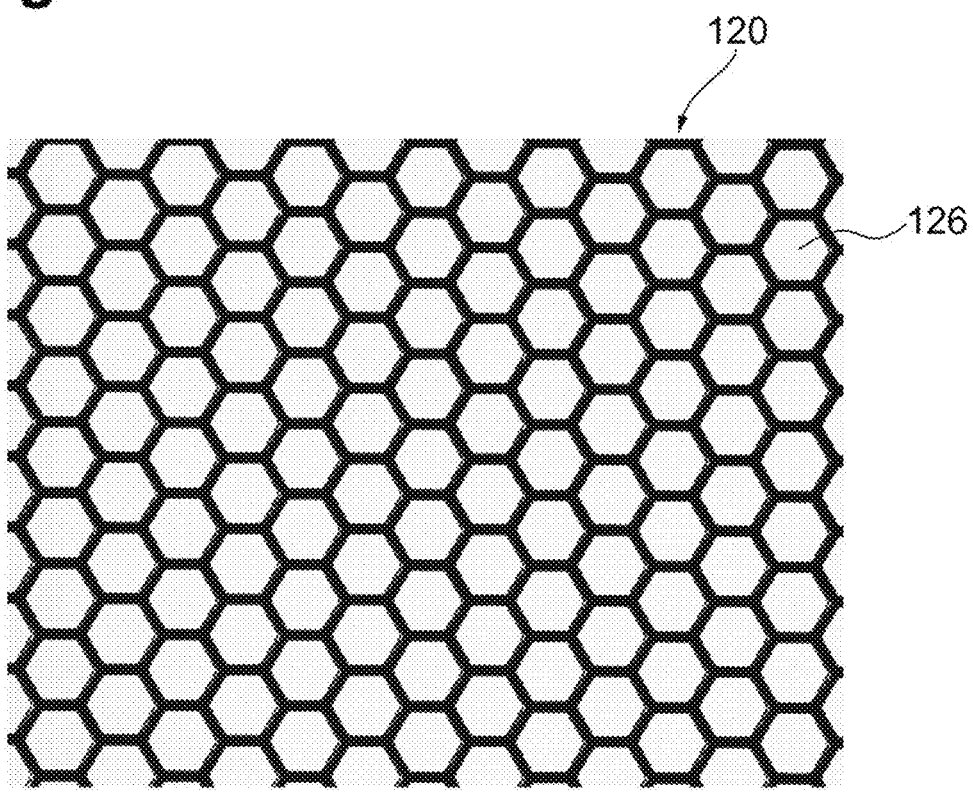
FIG. 21 is a diagram illustrating a modified example of a lens array.
Figure 22:
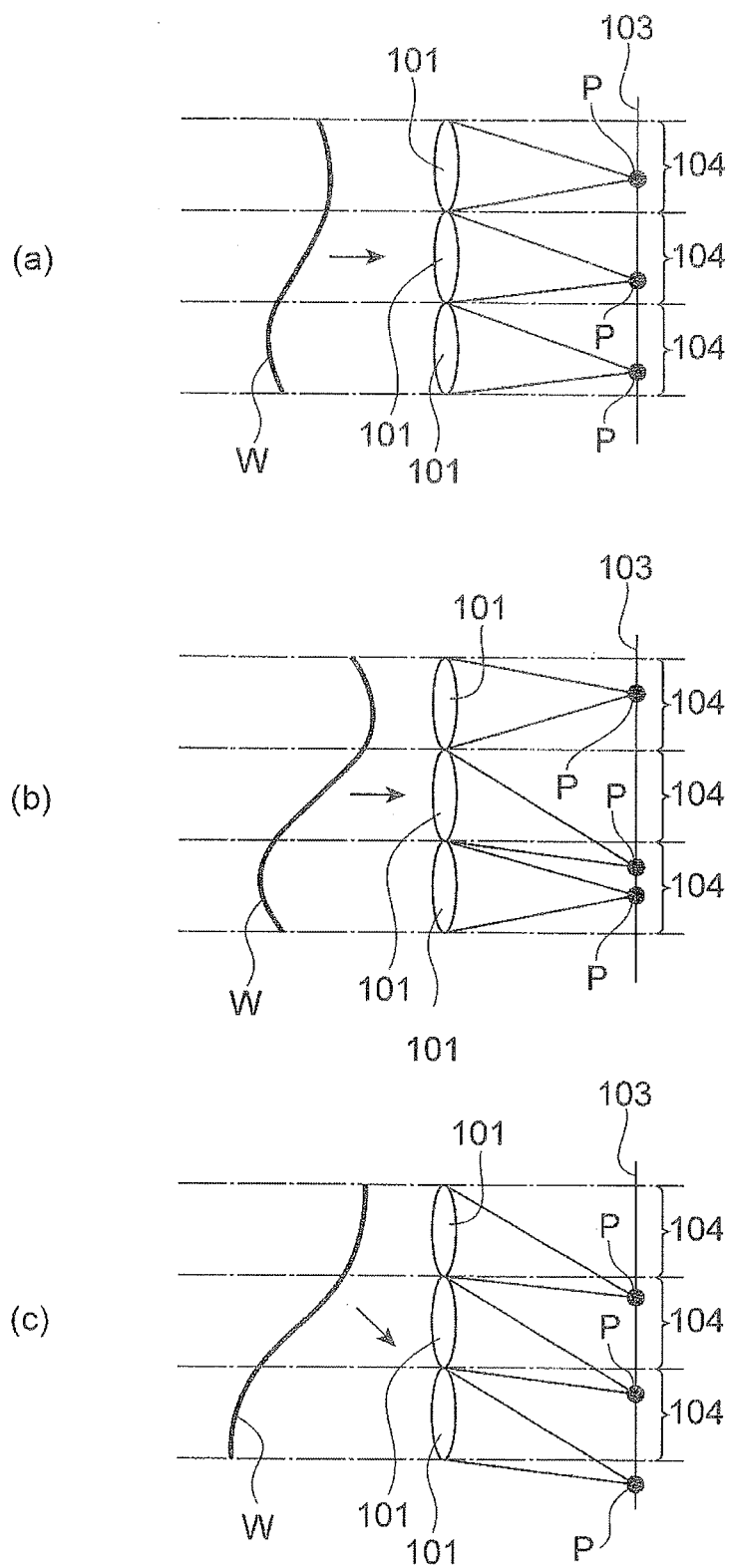
FIG. 22 is a diagram illustrating a correspondence relation between a plurality of lens and a plurality of converging spots when an optical image having a certain wavefront is incident on a wavefront sensor.

A correspondence relation specifying method for an adaptive optics system, an adaptive optics system, a program for an adaptive optics system, and a storage medium storing a program for an adaptive optics system according to an aspect of the present invention are not limited to the above-described embodiments and various other modifications are possible. For example, in the above-described embodiments and modified examples, an example of a form in which the plurality of lenses 124 are arranged as the lens array 120 of the wavefront sensor 12 in the two-dimensional lattice shape as illustrated in FIG. 3 is shown. However, the lens array of the wavefront sensor 12 is not limited to such a form. For example, as illustrated in FIG. 21, the lens array 120 may have a honeycomb structure in which a plurality of regular hexagonal lenses 128 are arranged without gaps.

INDUSTRIAL APPLICABILITY

According to a correspondence relation specifying method for an adaptive optics system, an adaptive optics system, a program for an adaptive optics system, and a storage medium storing a program for an adaptive optics system according to an aspect of the present invention, it is possible to precisely compensate for larger wavefront distortion by accurately specifying a correspondence relation between a converging spot of a wavefront sensor and a region on a modulation surface of a spatial light modulator to be controlled based on a position of the converging spot while an increase of the number of components and an increase of loss of light to be measured are suppressed.

REFERENCE SIGNS LIST

10 Adaptive optics system
11 Spatial light modulator
11a Modulation surface
11b Region
12 Wavefront sensor
13 Control unit
13a Storage region
14 Beam splitter
15, 16 Relay lens
17 Control circuit unit
18 Optical detection element
120 Lens array
122 Image sensor
124 Lens
L1 Optical image
P Converging spot

The invention claimed is:

1. A correspondence relation specifying method for an adaptive optics system, which includes a spatial light modulator configured to spatially modulate a phase of an optical image incident on a modulation surface including N (N is a natural number) two-dimensionally arranged regions and a wavefront sensor including a lens array having N two-dimensionally arranged lenses corresponding to the N regions and an optical detection element for detecting a light intensity distribution including M (M is a natural number and M≤N) converging spots formed by the lens array and configured to receive the optical image after the modulation from the spatial light modulator and which compensates for wavefront distortion by controlling a phase pattern displayed in the spatial light modulator based on a wavefront shape of the optical image obtained from the light intensity distribution, wherein a correspondence relation between the region of the spatial light modulator and the converging spot formed in the wavefront sensor is specified while the compensation for the wavefront distortion is executed, the correspondence relation specifying method comprising:
 a first detecting step of detecting the light intensity distribution through the optical detection element in a state in which a phase pattern for compensating for the wavefront distortion is displayed in a specific target region among the N regions of the spatial light modulator;
 a second detecting step of detecting the light intensity distribution through the optical detection element in a state in which a spatially non-linear phase pattern is displayed in the specific target region before or after the first detecting step; and
 a first specifying step of specifying a converging spot corresponding to the specific target region among the M converging spots based on a change in the light intensity distribution between the first detecting step and the second detecting step.

2. The correspondence relation specifying method for the adaptive optics system according to claim 1, further comprising:
 a third detecting step of detecting the light intensity distribution through the optical detection element in a state in which the phase pattern for compensating for the wavefront distortion is displayed in the specific target region and the spatially non-linear phase pattern is displayed in a specific target region separate from the specific target region; and
 a second specifying step of specifying a converging spot corresponding to the separate specific target region based on a change in the light intensity distribution between the second detecting step and the third detecting step.

3. The correspondence relation specifying method for the adaptive optics system according to claim 1, wherein, in the first detecting step, the phase pattern for compensating for the wavefront distortion is displayed in all of the N regions.

4. The correspondence relation specifying method for the adaptive optics system according to claim 1, wherein the wavefront distortion is compensated based on the wavefront shape obtained from the light intensity distribution detected in the second detecting step.

5. The correspondence relation specifying method for the adaptive optics system according to claim 1, wherein the spatially non-linear phase pattern displayed in the specific target region in the second detecting step includes a random distribution in which a distribution of magnitudes of phases is irregular.

6. The correspondence relation specifying method for the adaptive optics system according to claim 1, wherein the spatially non-linear phase pattern displayed in the specific target region in the second detecting step includes a defocus distribution which increases a diameter of the converging spot.

7. The correspondence relation specifying method for the adaptive optics system according to claim 1, wherein a plurality of regions which are not adjacent to each other among the N regions of the spatial light modulator are set in the specific target region.

8. An adaptive optics system comprising:
 a spatial light modulator configured to spatially modulate a phase of an optical image incident on a modulation surface including N (N is a natural number) two-dimensionally arranged regions;
 a wavefront sensor including a lens array having N two-dimensionally arranged lenses corresponding to the N regions and an optical detection element for detecting a light intensity distribution including M (M is a natural number and M≤N) converging spots formed by the lens array and configured to receive the optical image after the modulation from the spatial light modulator; and
 a control unit configured to compensate for the wavefront distortion by controlling a phase pattern displayed in the spatial light modulator based on a wavefront shape of the optical image obtained from the light intensity distribution,
 wherein the control unit acquires a first light intensity distribution through the light detection element in a state in which a phase pattern for compensating for the wavefront distortion is displayed in a specific target region among the N regions of the spatial light modulator while the compensation for the wavefront distortion is executed, acquires a second light intensity distribution through the optical detection element in a state in which a spatially non-linear phase pattern is displayed in the specific target region, and specifies a converging spot corresponding to the specific target region among the M converging spots based on a change between the first light intensity distribution and the second light intensity distribution.

9. A non-transitory computer readable storage medium for an adaptive optics system, which includes a spatial light modulator configured to spatially modulate a phase of an optical image incident on a modulation surface including N (N is a natural number) two-dimensionally arranged regions, a wavefront sensor including a lens array having N two-dimensionally arranged lenses corresponding to the N regions and an optical detection element for detecting a light intensity distribution including M (M is a natural number and M N) converging spots formed by the lens array and configured to receive the optical image after the modulation from the spatial light modulator, and a control unit configured to compensate for the wavefront distortion by controlling a phase pattern displayed in the spatial light modulator based on a wavefront shape of the optical image obtained from the light intensity distribution, wherein the program for the adaptive optics system causes the control unit to specify a correspondence relation between the region of the spatial light modulator and the converging spot formed in the wavefront sensor while the compensation for the wavefront distortion is executed, the program for the adaptive optics system causing the control unit to execute:

a first detecting step of detecting the light intensity distribution through the optical detection element in a state in which a phase pattern for compensating for the wavefront distortion is displayed in a specific target region among the N regions of the spatial light modulator;

a second detecting step of detecting the light intensity distribution through the optical detection element in a state in which a spatially non-linear phase pattern is displayed in the specific target region before or after the first detecting step; and a first specifying step of specifying a converging spot corresponding to the specific target region among the M converging spots based on a change in the light intensity distribution between the first detecting step and the second detecting step.

* * * * *